(12) United States Patent
Giese et al.

(10) Patent No.: US 12,359,243 B2
(45) Date of Patent: Jul. 15, 2025

(54) DNA ADDUCTOMICS BY MASS TAG PRELABELING

(71) Applicant: Northeastern University, Boston, MA (US)

(72) Inventors: Roger W. Giese, Hanover, MA (US); Poguang Wang, Westborough, MA (US)

(73) Assignee: Northeastern University, Boston, MA (US)

( * ) Notice: Subject to any disclaimer, the term of this patent is extended or adjusted under 35 U.S.C. 154(b) by 1108 days.

(21) Appl. No.: 17/307,607

(22) Filed: May 4, 2021

(65) Prior Publication Data

US 2021/0340603 A1    Nov. 4, 2021

Related U.S. Application Data

(60) Provisional application No. 63/019,647, filed on May 4, 2020.

(51) Int. Cl.
*C12Q 1/6806* (2018.01)

(52) U.S. Cl.
CPC ..... *C12Q 1/6806* (2013.01); *C12Q 2563/167* (2013.01); *C12Q 2565/627* (2013.01)

(58) Field of Classification Search
CPC ............ C12Q 1/6886; C12Q 2527/117; C12Q 2565/627
See application file for complete search history.

(56) References Cited

U.S. PATENT DOCUMENTS

| | | |
|---|---|---|
| 5,003,059 A | 3/1991 | Brennan |
| 5,174,962 A | 12/1992 | Brennan |
| 5,547,835 A | 8/1996 | Koster |
| 5,605,798 A | 2/1997 | Koster |
| 5,622,824 A | 4/1997 | K oster |
| 5,691,141 A | 11/1997 | Koster |
| 5,851,765 A | 12/1998 | Koster |
| 5,869,242 A | 2/1999 | Kamb |
| 5,872,003 A | 2/1999 | Koster |
| 6,043,031 A | 3/2000 | Koster et al. |
| 6,074,823 A | 6/2000 | Koster |
| 6,090,558 A | 7/2000 | Butler et al. |
| 6,140,053 A | 10/2000 | Koster |
| 6,194,144 B1 | 2/2001 | Koster |
| 6,197,498 B1 | 3/2001 | Koster |
| 6,221,601 B1 | 4/2001 | Koster et al. |
| 6,221,605 B1 | 4/2001 | Koster |
| 6,225,450 B1 | 5/2001 | Koster |
| 6,235,478 B1 | 5/2001 | Koster |
| 6,238,871 B1 | 5/2001 | Koster |
| 6,258,538 B1 | 7/2001 | Koster et al. |
| 6,268,144 B1 | 7/2001 | Koster |
| 6,277,573 B1 | 8/2001 | Koster |
| 6,300,076 B1 | 10/2001 | Koster |
| 6,428,955 B1 | 8/2002 | Koster et al. |
| 6,500,621 B2 | 12/2002 | Koster |
| 6,602,662 B1 | 8/2003 | Koster et al. |
| 6,613,509 B1 | 9/2003 | Chen |
| 6,699,689 B1 | 3/2004 | Kim et al. |
| 6,764,822 B1 | 7/2004 | Butler et al. |
| 7,198,893 B1 | 4/2007 | Koster et al. |
| 7,501,251 B2 | 3/2009 | Koster et al. |
| 2001/0038070 A1 | 11/2001 | Hausch et al. |
| 2002/0042112 A1 | 4/2002 | Koster et al. |
| 2002/0102556 A1 | 8/2002 | Laken et al. |
| 2002/0137046 A1 | 9/2002 | Koster |
| 2002/0168642 A1 | 11/2002 | Drukier |
| 2003/0027140 A1 | 2/2003 | Ju et al. |
| 2003/0129589 A1 | 7/2003 | Koster et al. |
| 2003/0228594 A1 | 12/2003 | Koster |
| 2004/0248098 A1 | 12/2004 | Inoko et al. |
| 2005/0064419 A1 | 3/2005 | Belouchi et al. |
| 2007/0202514 A1 | 8/2007 | Koster et al. |
| 2009/0023150 A1 | 1/2009 | Koster et al. |
| 2012/0102600 A1 | 4/2012 | Nadolska-Orczyk et al. |
| 2015/0050747 A1 | 2/2015 | Alocilja et al. |

OTHER PUBLICATIONS

Chen et al (Anal Chem 2019, 91, 7403-7410).*
Gruppi (Chemical Research Toxicology, 2015, pp. 1850-1860).*
Wang et al. (J Am Soc Mass Spectrom, 2015, 26:1713-1721).*
Wang et al., "DNA Adductomics by mass tag prelabeling," Rapid Commun Mass Spectrom, 35:e9095, pp. 1-13 (2021).

* cited by examiner

*Primary Examiner* — Sarae L Bausch
(74) *Attorney, Agent, or Firm* — Foley Hoag LLP; Dana M. Gordon; Lawrence P. Tardibono

(57) ABSTRACT

Disclosed is a method for detecting the presence of a DNA adduct in DNA. The method involves the pre-labeling of an adducted nucleotide in the DNA with a quaternary ammonium compound.

19 Claims, 18 Drawing Sheets

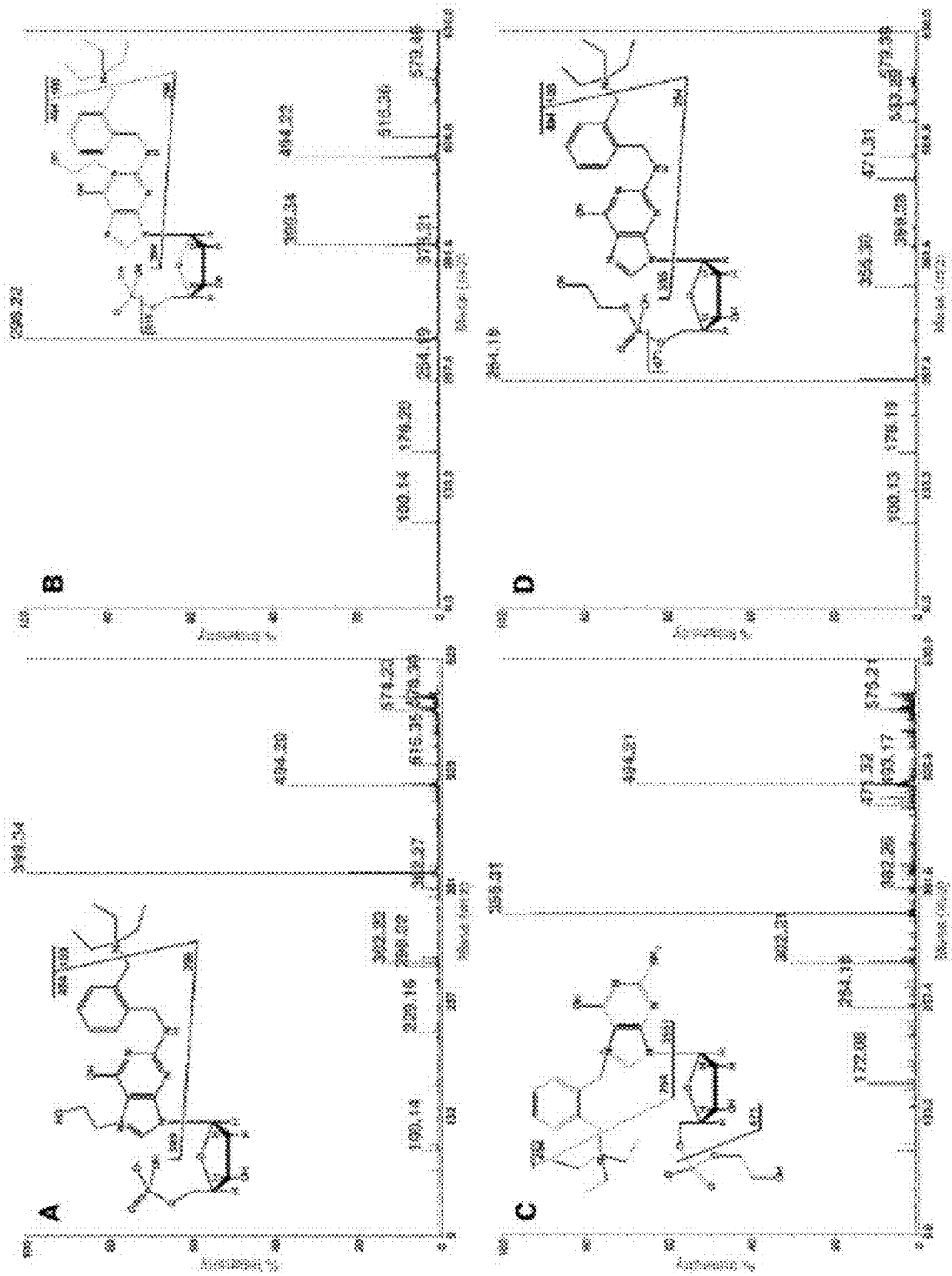
FIG. 7A, FIG. 7B, FIG. 7C, & FIG. 7D

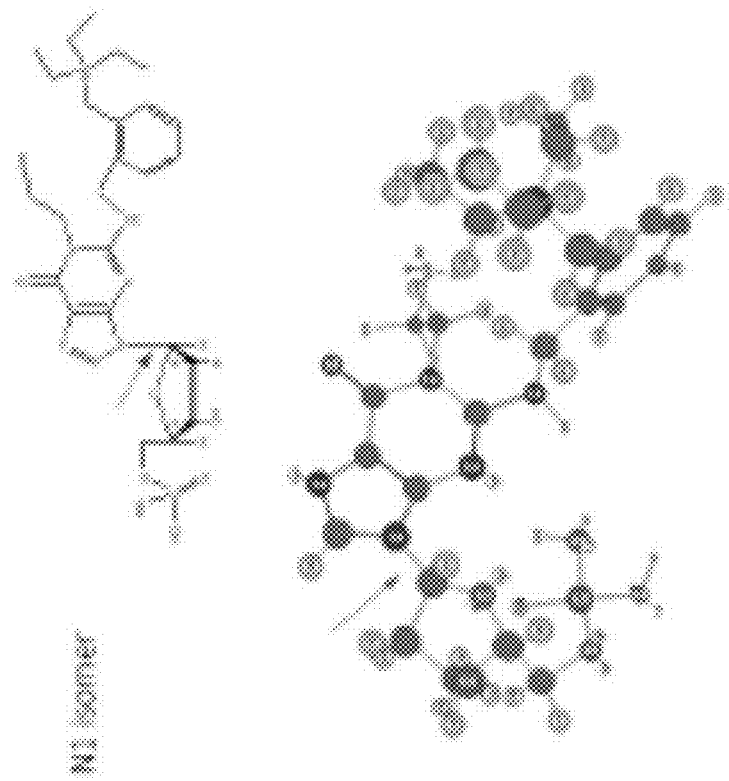
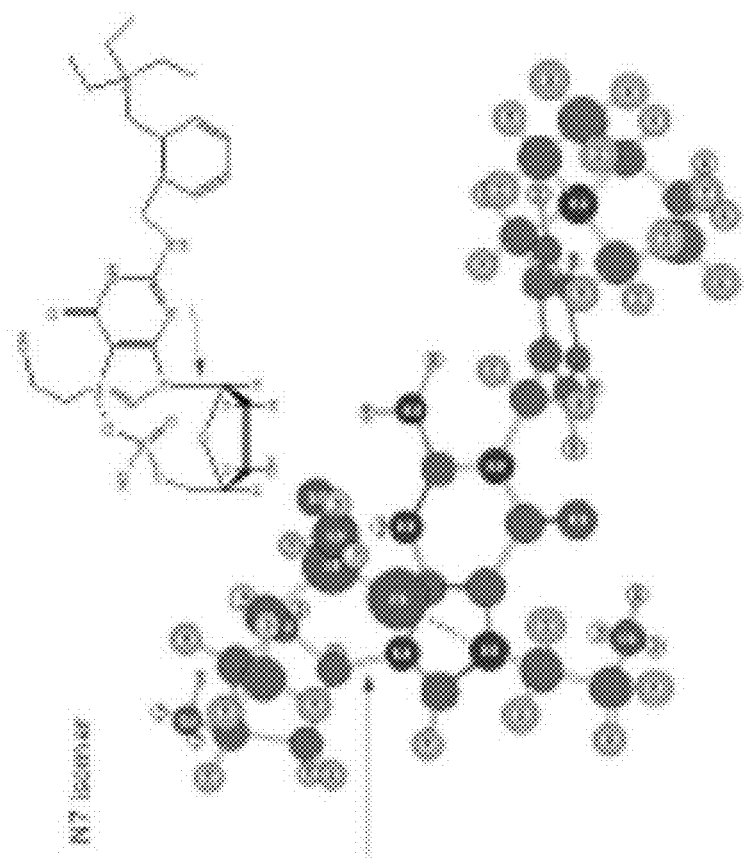
FIG. 8

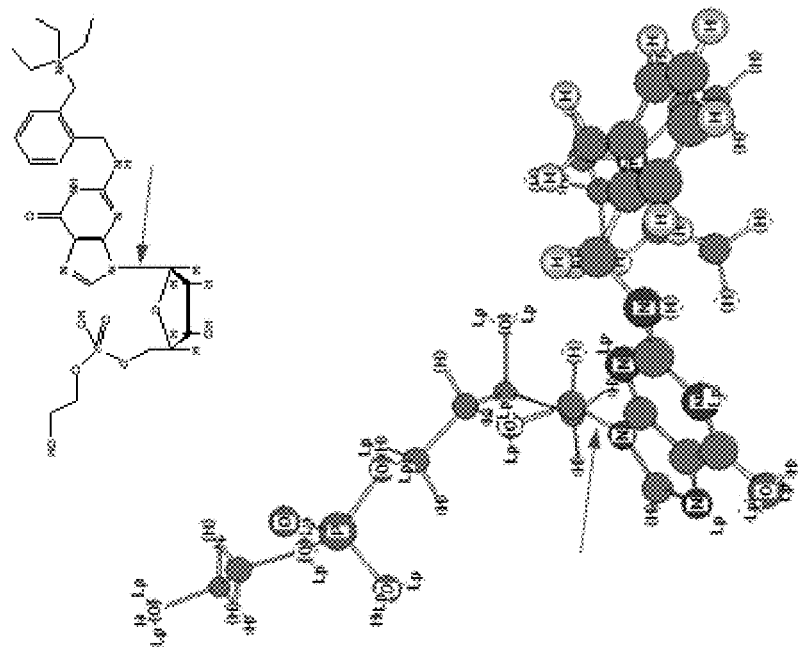
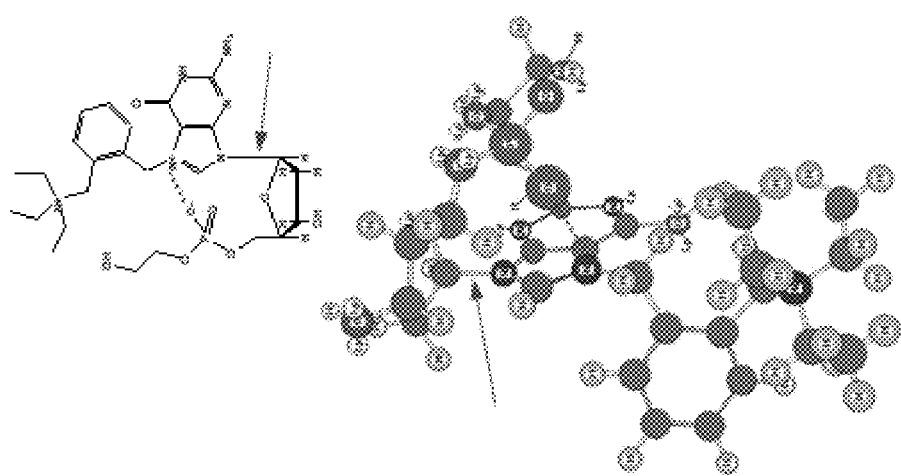
FIG. 13

DNA ADDUCTOMICS BY MASS TAG PRELABELING

RELATED APPLICATION

This application claims the benefit of priority to U.S. Provisional Patent Application No. 63/019,647, filed May 4, 2020.

GOVERNMENT SUPPORT

This invention was made with government support under Grant Number ES017198, awarded by the National Institutes of Health. The government has certain rights in the invention.

BACKGROUND

DNA adducts are damaged nucleotides in DNA as a consequence of its exposure to genotoxic agents or conditions. Measurement of multiple (especially many) DNA adducts in a single procedure is referred to as "DNA adductomics", a subject that has been reviewed [1-9]. In the leading analytical technique for this purpose, typically the following sequence of steps takes place starting with a biosample: (1) isolate the DNA; (2) digest it to deoxynucleosides enzymatically; (3) remove the enzymes and inject the deoxynucleosides into a UPLC-tandem mass spectrometer using mild CID conditions that release the sugar (116 u) as a neutral; and (4) observe peaks for adducts as protonated nucleobases, where UPLC is Ultra Performance Liquid Chromatography, and CID is collision-induced dissociation.

While this method is highly successful, including important extension in recent years to paraffin-fixed tissue samples [9-10], it has some shortcomings. First of all, response is adduct dependent. While a limit of quantitation (LOQ) of about 3 adducts in $10^9$ nucleotides can be reached using 2 mg of DNA for the most favorable (some bulky) adducts [9-14], limits of detection (LODs) can vary widely. For example, it was reported that LODs for different adducts ranged from 0.02 to 23.7 adducts in $10^8$ nucleotides, a 1,000-fold range [15]. Variation in ionization efficiency in the ion source along with differences in ease of sugar loss probably 85276519.2 explain most of this variation. Indeed, not all adducts give loss of sugar in the method [16], including phosphate adducts [17]. Second, polar adducts in the above sugar-loss method elute early in the usual reversed phase LC separation, where there is much noise, so they are not measured along with bulky adducts. Extra effort thereby may be necessary to measure polar adducts, such as two solid phase extractions prior to the LC separation even for a single, targeted adduct [18]. While 12 polar DNA adducts were measured in a single procedure [19-20], each adduct had to be collected separately from a first HPLC (High Performance Liquid Chromatography) separation prior to subsequent injection again into LC-MS. An API 3000 triple quadrupole mass spectrometer was employed with analyte-dependent detection parameters. The detection limit was about 1 adduct in $10^7$ nucleotides. Third, different adducts tend to require different LC mobile phase conditions and/or different MS conditions for optimum sensitivity. Fourth, the neutral loss of 116 u for adduct detection can come from noise, especially at lower adduct levels. Fifth, delayed addition of stable isotope nucleoside internal standard is usually employed, which can compromise absolute quantitation.

DNA adductomics also can be accomplished by mild acid depurination/LC-MS. This technique has been practiced, for example, by Hemeryck et al [21]. Four targeted guanine adducts (methyl, carboxymethyl, malonaldehyde, and methylhydroxypropano) were detected at an LOQ in the range of 4 to 22 adducts in $10^8$ nucleotides, based on spiking authentic, modified nucleobases at the ng level into 100 mg of DNA. Overall, in the samples tested (comprising chemically-treated calf thymus DNA samples and several colon tumor tissues) there was tentative detection of 20 other small adducts.

Another technique that is useful for DNA adductomics is "$^{32}$P-postlabeling", which has been reviewed [3,22]. In this method the following sequence of steps usually takes place once DNA has been isolated: (1) digest the DNA enzymatically to deoxynucleoside-3'-phosphates; (2) label the latter radio-enzymatically with [$^{32}$P]adenosine triphosphate; (3) conduct a chromatographic separation, usually by multidimensional TLC under conditions that first wash conventional deoxynucleotides out of a retention region of interest prior to migration of the adducts; and (4) measure DNA adducts as radioactive spots by storage phosphor imaging. This technique has been employed for many years and can provide high sensitivity. Its major disadvantages are that the yield of the labeling reaction is adduct dependent; it is difficult to incorporate internal standards; and it is not easy to establish the identity of a radioactive adduct TLC spot (or radioactive HPLC peak when this technique is used instead of TLC).

SUMMARY OF INVENTION

One aspect of the present invention provides a method for detecting the presence of a DNA adduct in DNA, comprising the following steps:
(1) reacting an adducted nucleotide in the DNA with a labeling precursor L1 to provide an adducted nucleotide labeled with label L;
(2) enzymatically digesting the DNA to provide a free adducted nucleotide comprising the label L; and
(3) detecting the free adducted nucleotide comprising the label L by mass spectrometry,
wherein the label L comprises a quaternary amine group.

Another aspect of the present invention provides a method for detecting the presence of a DNA adduct in DNA, comprising the following steps:
(1) reacting an adducted nucleotide in the DNA with a labeling precursor L1 to provide an adducted nucleotide labeled with label L;
(2) enzymatically digesting the DNA to provide a free adducted nucleotide comprising the label L;
(3) subjecting the free adducted nucleotide comprising the label L to conditions sufficient to provide the corresponding nucleoside comprising the label L; and
(4) detecting the nucleoside comprising the label L by mass spectrometry,
wherein the label L comprises a quaternary amine group.

Yet another aspect of the present invention provides a method for detecting the presence of a DNA adduct in DNA, comprising the following steps:
(1) reacting an adducted nucleotide in the DNA with a labeling precursor L1 to provide an adducted nucleotide labeled with label L;
(2) enzymatically digesting the DNA to provide a free adducted nucleotide comprising the label L;

(3) subjecting the free adducted nucleotide comprising the label L to conditions sufficient to provide the corresponding nucleoside comprising the label L;
(4) subjecting the nucleoside comprising the label L to conditions sufficient to provide the corresponding nucleobase comprising the label L; and
(5) detecting the nucleobase comprising the label L by mass spectrometry,
wherein the label L comprises a quaternary amine group.

BRIEF DESCRIPTION OF THE DRAWINGS

FIG. 7A: MALDI-TOF/TOF-MS spectra of CAX-hydroxyethyl-dGMP adduct 7A.

FIG. 7B: MALDI-TOF/TOF-MS spectra of CAX-hydroxyethyl-dGMP adduct 7B.

FIG. 7C: MALDI-TOF/TOF-MS spectra of CAX-hydroxyethyl-dGMP adduct 7C.

FIG. 7D: MALDI-TOF/TOF-MS spectra of CAX-hydroxyethyl-dGMP adduct 7D.

FIG. 8: Energy Minimization by MM2 method (Chem3D Pro 5.0: minimum RMS gradient of 0.1) of the N1 and N7 isomers of the CAX-hydroxyethyl-dGMP adducts.

FIG. 13: Configurations predicted by MM2 energy minimization method for the N2 and N7 isomers of the CAX-deoxyguanosine-monohydroxyethylphosphate. MM2 energy minimizing calculation predicts a negatively charged oxygen of the phosphate group close to the positively charged N7 position, while the N2 isomer assumes a more relaxed configuration. The arrows were added to help in viewing the drawings.

DETAILED DESCRIPTION OF THE INVENTION

Figure 1:
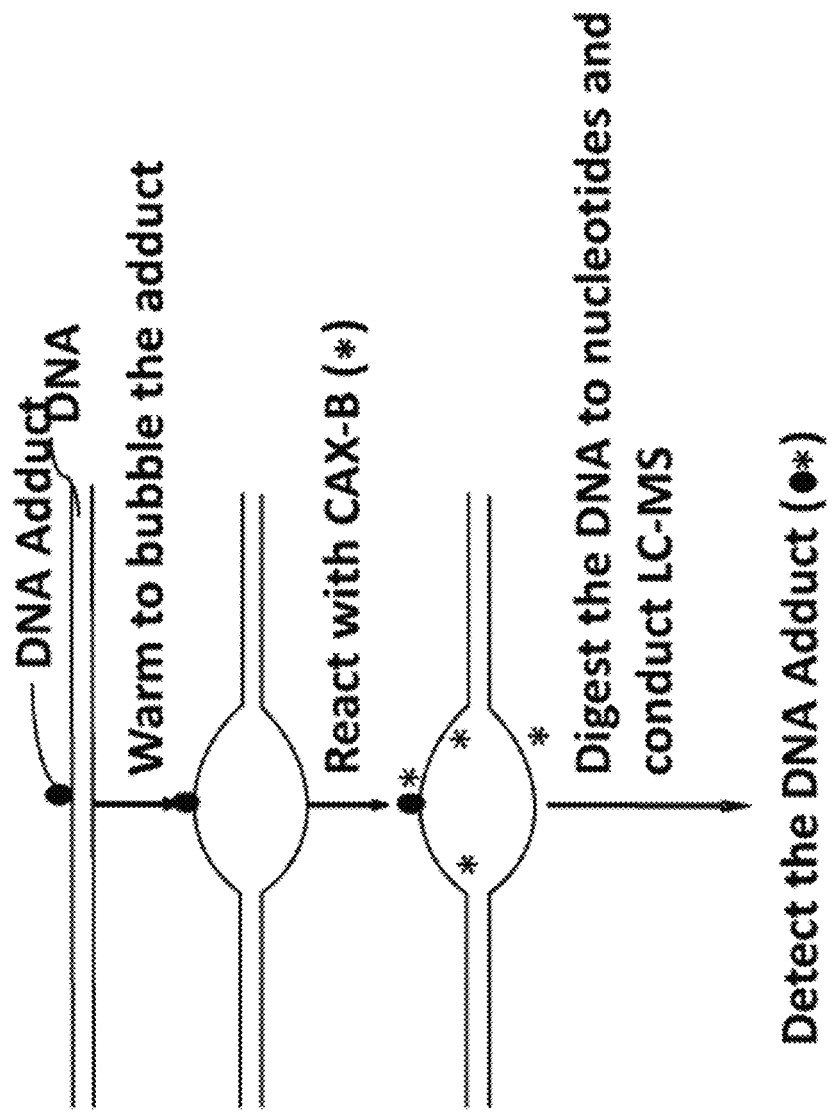
FIG. 1: A scheme for detecting a DNA adduct by Mass Tag Prelabeling with CAX-B (cationic xylyl bromide).

The present invention relates to a pre-labeling method for DNA adductomics. The method involves the pre-labeling of an adducted nucleobase with a quaternary ammonium cation.

The method of the present invention is advantageous in that it provides specific and sensitive detection of polar and nonpolar DNA adducts at the same time. The method converts polar adducts into nonpolar products for comprehensive adduct detection in a single procedure.

The method is practical in that it does not require a tedious method to remove a huge background of canonical DNA and nucleotides. Also, the method does not require radiolabeling, which a nonspecific method that provides no structural information about an adduct.

The method is applied to cell culture assays, animal studies, and clinical trials to provide simultaneous DNA assessment. The primary mechanisms behind biological events in these studies lie in the DNA and not what is usually measured at the biochemical level: e.g. proteins, lipids, carbohydrates and metabolites. Currently DNA assessment in these studies is missing or limited.

Additionally, the method is applied as a "Cancer Prevention Test", which allows for a subject to determine if any environmental chemicals are damaging their DNA. Such information then guides the subject to reduce their exposure to those chemicals. Currently there is no known diagnostic test where a subject can send a sample of blood or tissue for a comprehensive DNA adductomics test. The disclosed method provides such a test.

Exemplary Embodiments of the Invention

One aspect of the present invention provides a method for detecting the presence of a DNA adduct in DNA, comprising the following steps:
(1) reacting an adducted nucleotide in the DNA with a labeling precursor L1 to provide an adducted nucleotide labeled with label L;
(2) enzymatically digesting the DNA to provide a free adducted nucleotide comprising the label L; and
(3) detecting the free adducted nucleotide comprising the label L by mass spectrometry,
wherein the label L comprises a quaternary amine group.

In certain embodiments, the adducted nucleotide comprises a nucleobase and an adducted moiety X which is bonded to the nucleobase of the nucleotide.

In certain embodiments, the label L is covalently bonded to the nucleobase.

In certain embodiments, the label L is covalently bonded to the adducted moiety X.

In certain embodiments, the nucleobase is an adenine (A), cytosine (C), methyl-cytosine (MeC), guanine (G), thymine (T), or uracil (U).

In certain embodiments, the adducted moiety X is an oxo, alkyl, hydroxyl, hydroxyalkyl, benzyl, or aryl moiety. In other embodiments, the adducted moiety X is a hydroxymethyl or hydroxyethyl moiety. In other embodiments, the adducted moiety X is an oxo moiety. In other embodiments, the adducted moiety X is a hydroxyl moiety. In other embodiments, the adducted moiety X is an aryl moiety. In other embodiments, the adducted moiety X is a benzoquinone moiety. In other embodiments, the adducted moiety X is a benzopyrene moiety. In other embodiments, the adducted moiety X is an etheno moiety.

In certain embodiments, the labeling precursor L1 has the structure:

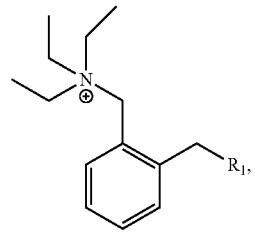

wherein $R_1$ is a leaving group.

In certain embodiments, $R_1$ is bromide, tosylate, or mesylate.

In certain embodiments, a nucleophilic moiety on the adducted nucleotide reacts with the labeling precursor L1 in step (1).

In certain embodiments, a nucleophilic moiety on the nucleobase reacts with the labeling precursor L1 in step (1).

In certain embodiments, a nucleophilic moiety on the adducted moiety X reacts with the labeling precursor L1 in step (1).

In certain embodiments, the nucleophilic moiety comprises an oxygen or nitrogen.

In certain embodiments, the nucleophilic moiety is a hydroxyl or amino group.

In certain embodiments, the label L has the following structure:

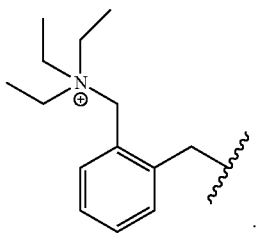 [SMILES: *Cc1ccccc1C[N+](CC)(CC)CC]

In certain embodiments, the labeling precursor L1 has the structure:

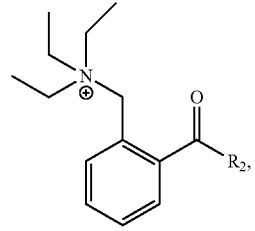

wherein $R_2$ is a leaving group.

In certain embodiments, $R_2$ is

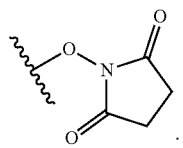 [SMILES: *ON1C(=O)CCC1=O]

In certain embodiments, a nucleophilic moiety on the adducted nucleotide reacts with the labeling precursor L1 in step (1).

In certain embodiments, a nucleophilic moiety on the nucleobase reacts with the labeling precursor L1 in step (1).

In certain embodiments, a nucleophilic moiety on the adducted moiety X reacts with the labeling precursor L1 in step (1).

In certain embodiments, wherein the nucleophilic moiety comprises an oxygen or nitrogen.

In certain embodiments, wherein the nucleophilic moiety is a hydroxyl or amino group.

In certain embodiments, wherein the label L has the following structure:

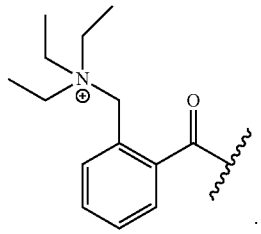 [SMILES: *C(=O)c1ccccc1C[N+](CC)(CC)CC]

In certain embodiments, the reaction in step (1) occurs at about 37° C. to 45° C.

In certain embodiments, the reaction in step (1) occurs at about 45° C.

In certain embodiments, the labeling precursor L1 substantially reacts with adducted nucleotides in the DNA relative to nucleotides comprising canonical nucleobases.

In certain embodiments, the labeling precursor L1 substantially reacts with adducted nucleotides in the DNA without substantially reacting with nucleotides comprising canonical nucleobases.

In certain embodiments, the label L comprises one or more isotopes of H, C, O, or N in an amount exceeding or less than the natural abundance.

In certain embodiments, the DNA is human DNA.

In certain embodiments, the adducted nucleotide comprises a hydroxyethylguanine, hydroxymethylcytosine, 8-oxoguanine, uracil glycol, 1,$N^6$-etheno-adenosine, $N^2$,3-ethenoguanine, or 1,$N^2$-ethenoguanine.

In certain embodiments, the detected nucleotide is Glycol-dUMP; hmdCMP; cdGMP; fapy-dAMP; fapy-dGMP; 8-oxo-dGMP; Et-dGMP; Et-fapy-dGMP; Et-dAMP; Bz-dGMP; Bz-fapy-dGMP; Bz-oxo-dGMP; Bz-dCMP; Bz-dmCMP; Bz-TMP; Bz-dAMP; Bz-hmCMP; hydroxyethyl-dGMP; hydroxyethyl-fapy-dGMP; hydroxyethyl-dAMP; hydroxyethyl-dCMP; SO-dGMP; SO-dA; SO-dC; SO-fapy-dGMP; SO-TMP; B(a)P-dGMP; BQ-dCMP; BQ-dmCMP; BQ-hmdCMP; etheno-dGMP; etheno-dAMP; or etheno-fapy-dA.

In certain embodiments, the quaternary amine group comprises three alkyl groups. In certain embodiments, the alkyl groups are select from methyl, ethyl, isopropyl.

Another aspect of the present invention provides a method for detecting the presence of a DNA adduct in DNA, comprising the following steps:
(1) reacting an adducted nucleotide in the DNA with a labeling precursor L1 to provide an adducted nucleotide labeled with label L;
(2) enzymatically digesting the DNA to provide a free adducted nucleotide comprising the label L;
(3) subjecting the free adducted nucleotide comprising the label L to conditions sufficient to provide the corresponding nucleoside comprising the label L; and
(4) detecting the nucleoside comprising the label L by mass spectrometry,
wherein the label L comprises a quaternary amine group.

Yet another aspect of the present invention provides a method for detecting the presence of a DNA adduct in DNA, comprising the following steps:
(1) reacting an adducted nucleotide in the DNA with a labeling precursor L1 to provide an adducted nucleotide labeled with label L;
(2) enzymatically digesting the DNA to provide a free adducted nucleotide comprising the label L;
(3) subjecting the free adducted nucleotide comprising the label L to conditions sufficient to provide the corresponding nucleoside comprising the label L;
(4) subjecting the nucleoside comprising the label L to conditions sufficient to provide the corresponding nucleobase comprising the label L; and
(5) detecting the nucleobase comprising the label L by mass spectrometry,
wherein the label L comprises a quaternary amine group.

Still another aspect of the present invention provides a method for detecting the presence of a DNA adduct in DNA, comprising the following steps:
(1) reacting an adducted nucleobase in the DNA with a labeling precursor L1 to provide an adducted nucleobase labeled with label L;
(2) subjecting the DNA to neutral thermal hydrolysis to provide a free adducted nucleobase labeled with label L; and
(3) detecting the free adducted nucleobase labeled with label L by mass spectrometry,
wherein the label L comprises a quaternary amine group.

Another aspect of the present invention provides a method for determining the likelihood of a subject developing a cancer.

In certain embodiments, the determination is based on the quantity and identity of DNA adducts detected in the DNA of the subject.

The subject invention is also intended to include all isotopes of atoms occurring on the compounds disclosed herein. Isotopes include those atoms having the same atomic number but different mass numbers. By way of general example and without limitation, isotopes of hydrogen include deuterium (D). Any notation of a carbon in structures throughout this application, when used without further notation, are intended to represent all isotopes of carbon, such as $^{12}C$, $^{13}C$, or $^{14}C$. Any notation of a hydrogen in structures throughout this application, when used without further notation, are intended to represent all isotopes of hydrogen, such as $^1H$, $^2H$, or $^3H$. Isotopically-labeled compounds can generally be prepared by conventional techniques known to those skilled in the art using appropriate isotopically-labeled reagents in place of the non-labeled reagents employed.

Definitions

The term "DNA Adduct" as used herein refers to chemically modified DNA or chemically modified nucleotides in the DNA due to exposure to genotoxic agent (e.g. mutagenic or carcinogenic agents) and their reactive metabolites, or genotoxic conditions. This damage affects DNA repair and/or replication and may lead to carcinogenesis.

Materials and Methods

N-(2-(Bromomethyl)benzyl)-N,N-diethylethanaminium bromide, that we designate as CAX-B, was synthesized as described [23]. Benzyl bromide, methanesulfonic acid ethyl ester, chloroacetaldehyde, 1-(2-chloroethyl)-3-cyclohexyl-1-nitrosourea (Lomustine), styrene oxide, bromoacetic acid, calf thymus DNA, triethylamine, and a-cyano-4-hydroxy-cinnamic acid (CCA) were from Sigma (St. Louis, Mo.). Microcentrifuge tubes, pipette tips, HPLC grade methanol, and acetonitrile (ACN) were from Fisher Scientific (Pittsburgh, Pa.). All materials were used as received. CCA Matrix Solution was 5 mg/mL in 50% ACN (v/v). Amicon Ultra Centrifuge Filters, Ultracel-3K, were from Millipore (Billerica, Mass.). DNA adducts in calf thymus DNA were formed in test tube experiments as described: benzyl, ethyl and hydroxyethyl [24], etheno [25], styrene oxide [26], benzo[a]pyrene [27], and benzoquinone [28]. Oxidative DNA adducts were generated from treatment of DNA with bromoacetic acid: 100 μL of calf thymus DNA at 0.5 mg/mL was mixed with 2 μL of bromoacetic acid, and kept at 37° C. for 2 h. Brain tissues were obtained from the NIH NeuroBioBank at the University of Maryland. Frozen postmortem tissues from three neurologically normal individuals, UMB4638, UMB1465, and UMB4643, were obtained as part of a previous study [29]. Samples were processed according to a standardized protocol under the supervision of the NIH NeuroBioBank ethics guidelines.

DNA Extraction

DNA was extracted from human skin obtained under IRB approval using the QIAamp DNA Mini Kit (Cat No. ID: 51304).

Instrumentation and Calculations

The MALDI-TOF/TOF-MS was a model 5800 from AB-SCIEX (Framingham, Mass.). The resolution is ~20,000 in the TOF positive Reflectron mode with a delay time of 120 ns, and ~3,000 in the TOF/TOF positive 1 kV mode with CID gas off and a 1 Da isolation window. The capillary LC (CapLC) system for detection of CAX-labeled DNA adducts by CapLC-MALDI-TOF-MS or CapLC-MALDI-TOF/TOF-MS was a Dionex Ultimate (Thermo Scientific). Column: 0.3×150 mm, 2 μm Acclaim PepMed C18. Mobile phase solvent: A, 8% ACN (v/v); and B, ACN. Mobile phase conditions: 3% B for 0-4 min, then up to 90% B over 60 min at 4 μL/min. Post LC steps: collect 4 droplets/min onto a MALDI plate (384 format), manually add 0.5 μL of CCA Matrix Solution to each spot, and conduct MALDI-TOF-MS or MALDI-TOF/TOF-MS.

For detection of DNA adducts by LC-ESI-MS2, a Dionex Ultimate UPLC fitted with an Aquasil C18 column (1×250 mm, 5 μm) was coupled to an LTQ Orbitrap XL: 0.1% formic acid for channel A and 0.1% formic acid, 99.9% acetonitrile for channel B, 8% B for 0-3 min, and up to 90% B over 40 min at 50 μL/min; ESI capillary temperature of 275° C., sheath gas flow of 10, source voltage of 4.9 kV, source current of 100 μA, capillary voltage of 49V, and tube lens of 95V; full-scan MS spectra (300-1500 m/z) at a resolution of 30,000, and two micro-scans of a maximum injection time of 80 ms, followed by top 2 data-dependent ion trap MS/MS with CID energy at 28, and a 2 Da isolation window. Energy minimization of gas phase ions was done by the MM2 method (Chem3D Pro 5.0: minimum RMS gradient of 0.1).

CAX-Prelabeling takes place as illustrated in FIG. 1, and relies on the tendency of DNA adducts to distort/destabilize local structure of ds-DNA into what is sometimes referred to as a "DNA bubble". In principle, this can make this region of DNA, and its resident DNA adduct, more susceptible to further reaction, as with an alkylating mass tag, as practiced here. We selected CAX-B (cationic xylyl bromide) as the mass tag for this endeavor. As reported before, CAX-B can enable highly sensitive, specific detection, especially in a tandem mass spectrometer, since it is an anchimeric-assisted, neutral loss mass tag [23]. Thereby it gives an analyte-characteristic $[M+H-N(CH_2CH_3)_3]+$ under mild collision-induced dissociation (CID) conditions. An analyte-characteristic ion arises since a neutral loss group is built into the tag.

To conduct CAX-Prelabeling, we react DNA with CAX-B at 45° C. (to promote DNA bubbling), and in the presence of triethylamine (to enhance labeling of active hydrogen sites. At the end of the 2 hour reaction, the DNA is washed by filtration to remove residual CAX-B and its hydrolysis products, and digested enzymatically to nucleotides. This mixture is applied to an OASIS HLB cartridge, where non-tagged nucleotides, as highly polar anions, elute readily. CAX-labeled adducts and CAX-labeled canonical nucleotides tend to be retained since they are zwitterions, and CAX has some nonpolar structure. Subsequently, aqueous methanol is applied to the cartridge and the eluted zwitterions are analyzed by UPLC-tandem MS. DNA adducts tend to stand out in MS2 due to the loss of both the triethylamine moiety (a characteristic of CAX), and the phosphate-deoxyribose moiety, under CID conditions.

Abbreviations

Glycol-dUMP, glycol-deoxyuridine-monophosphate; dUMP, deoxyuridinemonophosphate; hmdCMP, 5-hydroxymethyldeoxycytidine-monophosphate; cdGMP, 8,5'-cyclo-2'-deoxyguanosine-monophosphate; fapy-dAMP, 4,6-diamino-5-formamidopyrimidine-deoxyadenosine—monophosphate; fapy-dGMP, 2,6-diamino-4-hydroxy-5-formamidopyrimidine-deoxyguanosine—monophosphate; 8-oxo-dGMP, 8-oxo-deoxyguanosine-monophosphate; Et-dGMP, ethyl—deoxyguanosinemonophosphate; Et-fapy-dGMP, ethyl-2,6-diamino-4-hydroxy-5-formamidopyrimidine-deoxyguanosine-monophosphate; dAMP, deoxyadenosine-monophosphate; Et-dAMP, ethyl deoxyadenosine-monophosphate; Bz-dGMP, benzyl-deoxyguanosinemonophosphate; Bz-fapy-dGMP, benzyl-2,6-diamino-4-hydroxy-5-formamidopyrimidinedeoxyguanosine-monophosphate; Bz-oxo-dGMP, benzyl-oxo-deoxyguanosinemonophosphate; Bz-dCMP, benzyl-deoxycytidine-monophosphate; Bz-dmCMP, benzyl-deoxymethylcytidine-monophosphate; Bz-TMP, benzyl-thymidinemonophosphate; Bz-dAMP, benzyl-deoxyadenosine—monophosphate; Bz-hmCMP, benzyl-hydroxymethylcytidine-monophosphate; hydroxyethyl-dGMP, 2-hydroxyethyldeoxyguanosine-monophosphate; hydroxyethyl-fapy-dGMP, hydroxyethyl-2,6-diamino-4-hydroxy-5-formamidopyrimidine-deoxyguanosine-monophosphate; hydroxyethyl-dAMP, hydroxyethyl-deoxyadenosine-monophosphate; hydroxyethyl-dCMP, hydroxyethyl-deoxycytidine-monophosphate; SO-dGMP, styrene oxidedeoxyguanosine-monophosphate; SO-dA, styrene oxide-deoxyadenosinemonophosphate; SO-dC, styrene oxide-deoxycytidine-monophosphate; SO-fapy-dGMP, styrene oxide-2,6-diamino-4-hydroxy-5-formamidopyrimidine-deoxyguanosinemonophophosphate; SO-TMP, styrene oxide-thymidine-monophosphate; B(a)P-dGMP, benzo(a) pyrene-deoxyguanosine monophosphate; BQ-dCMP, benzoquinonedeoxycytidine-monophosphate; BQ-dmCMP, benzoquinone-deoxycytidinemonophosphate; BQ-hmdCMP, benzoquinone-hydroxymethyldeoxycytidinemonophosphate; etheno-dGMP, etheno-deoxyguanosine-monophosphate; etheno-dAMP, etheno-deoxyadenine-monophosphate; etheno-fapy-dA, etheno-2,6-diamino-4-hydroxy-5-formamidopyrimidine-deoxyguanosine-monophosphate; ACN, acetonitrile; MALDI, matrix assisted laser desorption ionization; LC, liquid chromatography; CCA, acyano-4-hydroxycinnamic acid; CAX-B, N-(2-(bromomethyl)benzyl)-N,Ndiethylethanaminium bromide or cationic xylylbromide; CCA, a-cyano-4-hydroxycinnamic acid; MALDI, matrix assisted laser desorption ionization; and LC, liquid chromatography.

Example 1. Detection of DNA Adducts in a Nucleotide Form Via CAX-B Prelabeling/Digestion/MS CAX-B in 50% ACN (20 mg/mL), with $Et_3N$ (30 μL/mL), is mixed 1:2 (v/v) with a solution of DNA (100 μL at ~1 mg/mL in water). After 2 h at 45° C., the reaction mixture is loaded into an Amicon Ultra Centrifuge Filter (Millipore, UFC500396, 0.5 mL, 3000 NMWL), followed by centrifugation at 12,000 rpm for 15 min (13,800×g, Thermo-Fisher AccuSpin Micro 17) and washing similarly with 5×300 μL of 10% ACN in water (to remove low mass chemical background), while retaining DNA. The retained DNA is recovered by rinsing the internal area of the filter with 50 μL of water, and centrifuging the reversed filter for 3 min. The recovered sample solution is subjected to a two-step enzymatic digestion (nuclease P1 and phosphodiesterase I) as described [30], loaded onto an OASIS HLB 1 cc cartridge (Waters, WAT094225), washed with 2×1 mL of water (to remove untagged normal nucleotides), and eluted with 0.8 mL methanol:water, 8:2, v/v. After evaporation in a Speed Vac (Thermo, SPD111V), redissolving in 12 μL of ACN: water, 6:94, and centrifuging at 12,000 rpm for 5 min, 5 μL of the clear solution is injected into the above LC-MALDI-TOF/TOF-MS, or LC-LTQ Orbitrap XL system. Alternatively, 2 μL were combined with 2 μL of matrix and 0.7 μL was subjected to MALDI-TOF/TOF-MS.

Example 2. Detection of DNA Adducts in a Nucleoside Form Via CAX-B Prelabeling/Digestion/MS The above sample after evaporation in a Speed Vac is re-dissolved in 50 μL of 1 mM Tris pH 8.9 containing 50% glycerol and alkaline phosphatase. After incubation for 18 h at 37° C., the solution is filtered as above on a Millipore 3000 NMWL, followed by washing with 2×50 μL of water. The combined filtrate is re-dissolved in 20 μL of ACN:water, 6:94 v/v, centrifuged as above, and 5 μL is injected into one of the above mass spectrometer systems.

Example 3. Detection of DNA Adducts in a Nucleobase Form Via CAX-B Prelabeling/Digestion/Neutral Thermal Hydrolysis/MS The above combined re-dissolved filtrate of labeled nucleosides is diluted to 100 μL with phosphate buffer, 50 mM, pH 7.0, and kept in a sealed tube for 72 h at 37° C. The tube is then heated at 95° C. for 4 h. After passing through an OASIS MAX solid phase extraction cartridge, and washing with 2×100 μL of 50% ACN, the combined filtrates are evaporated, re-dissolved in 20 μL of 6:94, v/v, ACN:water, and 5 μL is injected into one of the above mass spectrometer systems.

Example 4. Detection of DNA Adducts by CAX-X Mass Tag Prelabeling, where X in CAX-X Provides an Aniline (Phenylamino), Benzaldehyde, Active Ester (e.g. N-Hydroxysuccinimide Ester), Epoxide, Isothiocyanate, Hydrazide, or an Oxyamino $(RONH_2)$ Reactive Group CAX-X is reacted with DNA in the same way as CAX-B, except that sodium cyanoborohydride is present when X is aniline, and that triethylamine may or may not be present in general) and the following steps as above are the same as well, to yield a labeled nucleotide, nucleoside, or nucleobase product for detection by MS.

Example 5. Detection of DNA Adducts by Isotopic CAX-B (I-CAX-B) Mass Tag Prelabeling or I-CAX-X Mass Tag Prelabeling I-CAX-B can be prepared from an isotopic component reagent having one or more atoms of $^2H$, $^{13}C$, $^{15}N$, or $^{18}O$. Mass Tag Prelabeling is then conducted with about a 1:1 mixture of CAX-B and I-CAX-B, to increase assay specificity (formation of peak pairs). I-CAX-X can be similarly prepared and used.

Example 6. 8-Oxoguanine

Figures 2A, 2B:
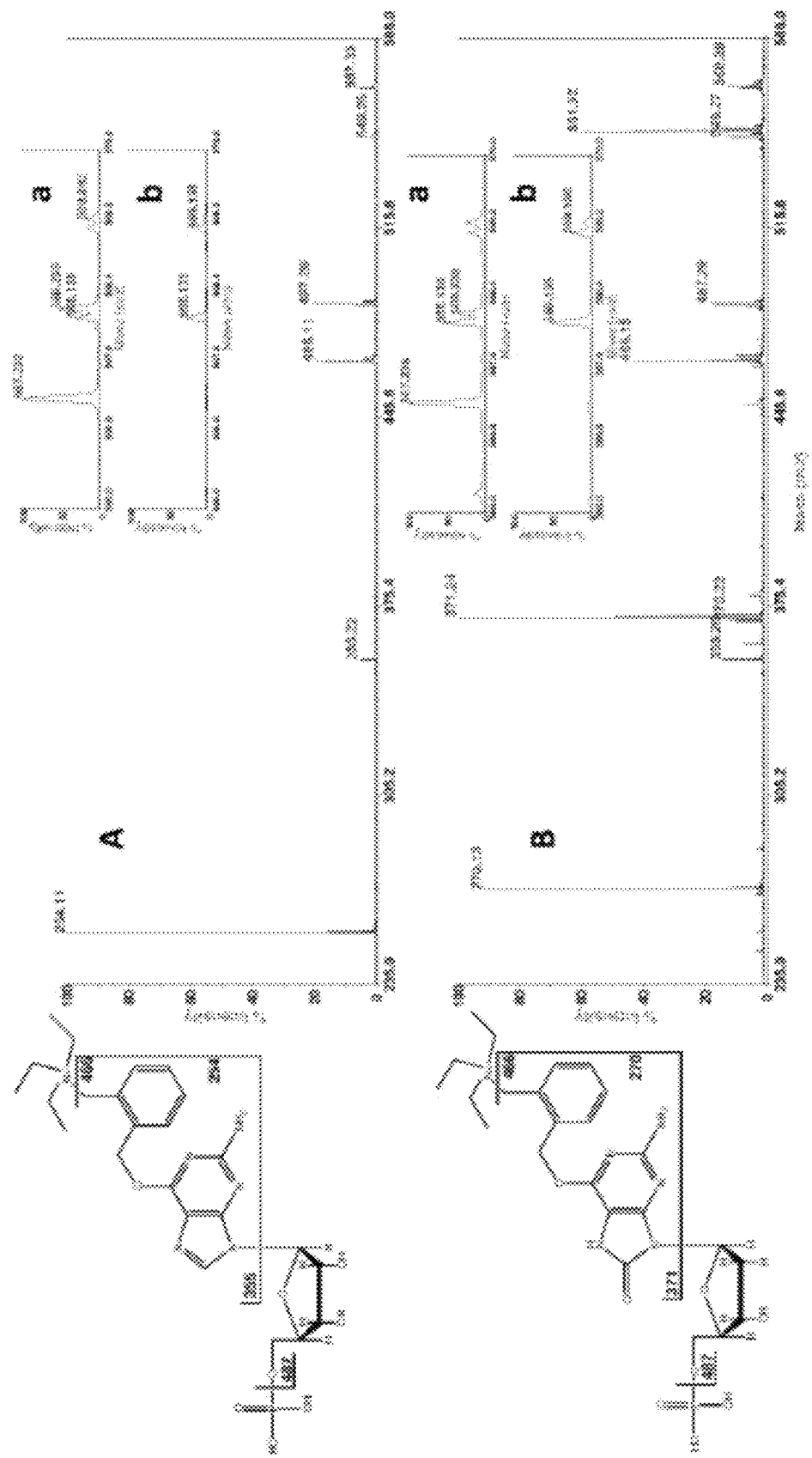
FIG. 2A: MALDI-TOF/TOF-MS spectra and peak assignments for CAX-labeled GMP, having the same precursor mass ($C_{24}H_{36}N_6O_8P+$, exact mass: 567.233), and derived from calf thymus DNA (which contains some RNA) according to the scheme shown in FIG. 1. Inset: a, precursor ion at m/z 567.232, along within M+1 and M+2 isotopes, by MALDI-TOF-MS; inset b, corresponding matrix blank. Peak assignments for the MALDI-TOF/TOF-MS spectrum of GMP are shown at the left.
FIG. 2B: MALDI-TOF/TOF-MS spectra and peak assignments for CAX-labeled 8-oxo-dGMP, having the same precursor mass ($C_{24}H_{36}N_6O_8P+$, exact mass: 567.233), and derived from calf thymus DNA (which contains some RNA) according to the scheme shown in FIG. 1. Inset: corresponding data for 8-oxo-dGMP are shown in (a) and (b), along with corresponding MS2 data and interpretation.

Detection of 8-oxo-dGMP in commercial calf thymus DNA by CAX-Prelabeling with LC-MALDI-TOF/TOF MS is shown in FIG. 2B, along with detection of its isomer, GMP, in FIG. 2A. (We have never encountered a DNA sample completely devoid of RNA.) For both spectra, the precursor ion at 567 Da is selected for CID. These precursor ion spectra are shown in the insets along with the CCA matrix blank spectra. In FIG. 2A, CAX-GMP is detected as four product ions (m/z 254, 355, 466 and 487), while CAX-8-oxo-dGMP is detected similarly in FIG. 2B by ions at m/z 270, 371, 466 and 487. As seen, the former pair of ions in each case (at lower masses) distinguishes these compounds. The fragmentation explaining these ions is shown in this figure. The placement of the CAX moiety on the 06 position of guanine in each case is arbitrary. Perhaps the 8-oxo atom of CAX-8-oxo-dGMP, by an inductive mechanism, enhances cleavage of the glycolytic bond relative to the corresponding bond in CAX-GMP when [M+H–neutral fragment]+ is generated (m/z 371 in B is much more intense than m/z 355 in A). The HPLC conditions separated CAX-labeled 8-oxo-dGMP and GMP (data not shown, retention times 17.7 and 20.3 min respectively). While these compounds have similar polarities, their unique product ion spectra distinguish them. We made no effort to quantify the compounds.

Figures 3A, 3B:
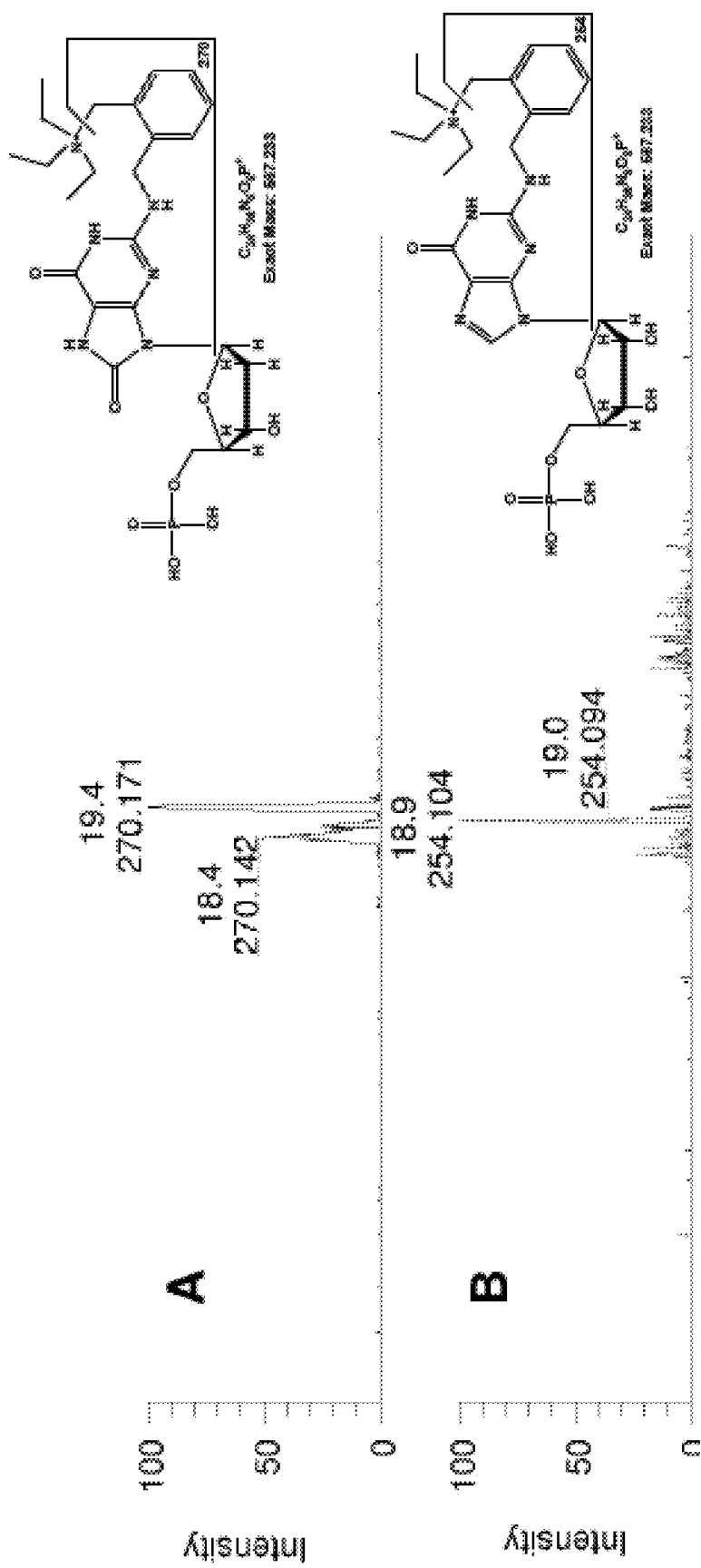
FIG. 3A: Detection of nucleotides in human skin DNA using an LC-LTQ Orbitrap in the SIM mode from full scan MS1 or MS2 data. SIM/MS2 of CAX-8-oxo-dGMP (monitoring the product ion at m/z 270 from 567 Da).
FIG. 3B: Detection of nucleotides in human skin DNA using an LC-LTQ Orbitrap in the SIM mode from full scan MS1 or MS2 data. SIM/MS2 of CAX-GMP (monitoring the product ion at m/z 254 from 567 Da).
Figures 3C, 3D:
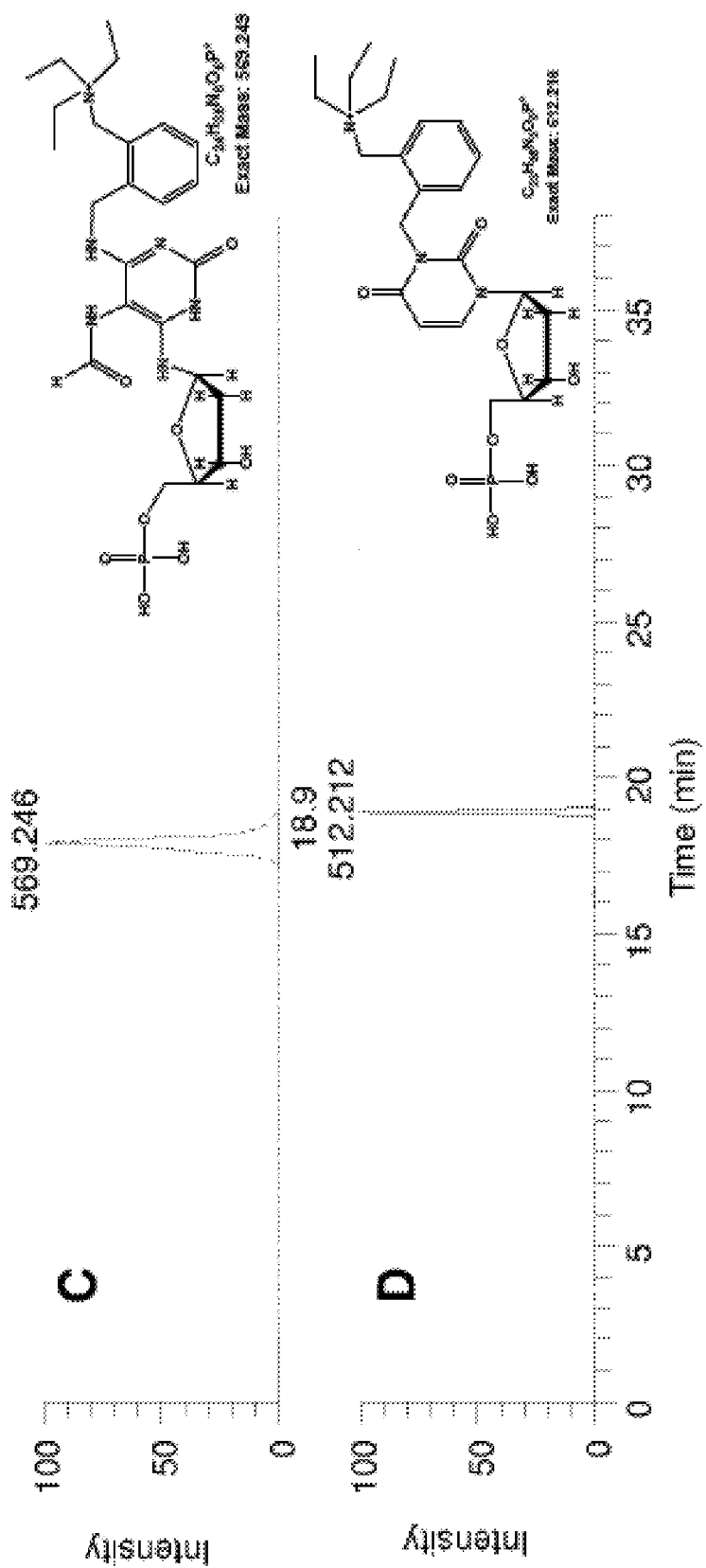
FIG. 3C: Detection of nucleotides in human skin DNA using an LC-LTQ Orbitrap in the SIM mode from full scan MS1 or MS2 data. SIM/MS1 of CAX-fapy-dGMP (m/z 569, exact mass 569.249).
FIG. 3D: Detection of nucleotides in human skin DNA using an LC-LTQ Orbitrap in the SIM mode from full scan MS1 or MS2 data. SIM/MS1 of CAX-dUMP (m/z 512, exact mass 512.216).

FIG. 3 shows the detection of 8-oxo-dGMP along with three other modified nucleotides that we detected when CAX-Prelabeling was applied to DNA from a sample of human skin. The selected ion monitoring (SIM) mass chromatograms are extracted from LC-LTQ Orbitrap full scan data in either the MS1 or MS2 mode. The four nucleotides detected, as CAX derivatives, are as follows: A, 8-oxo-dGMP; B, GMP; C, fapy-dGMP; and D, dUMP. An effective LC retention time (around 19 min, escaping the early noise region while maintaining resolution) is seen for all of these compounds, largely due to the moderate nonpolar structure of the CAX moiety, and the fact that the CAX-labeled nucleotides are zwitterions. Note that CAX-GMP (tR=18.9 min) once again (LC-MALDI above, LC-Orbitrap here) is readily separated from CAX-8-oxo-dGMP (tR=19.4 min), even though they are isomers. Perhaps the peak for CAX-fapy-dGMP (C) is broader since, relative to the other compounds (A, B, D), this compound is less compact in a way that gives it some surfactant behavior.

Example 7. Uracil-Glycol

Figure 4:
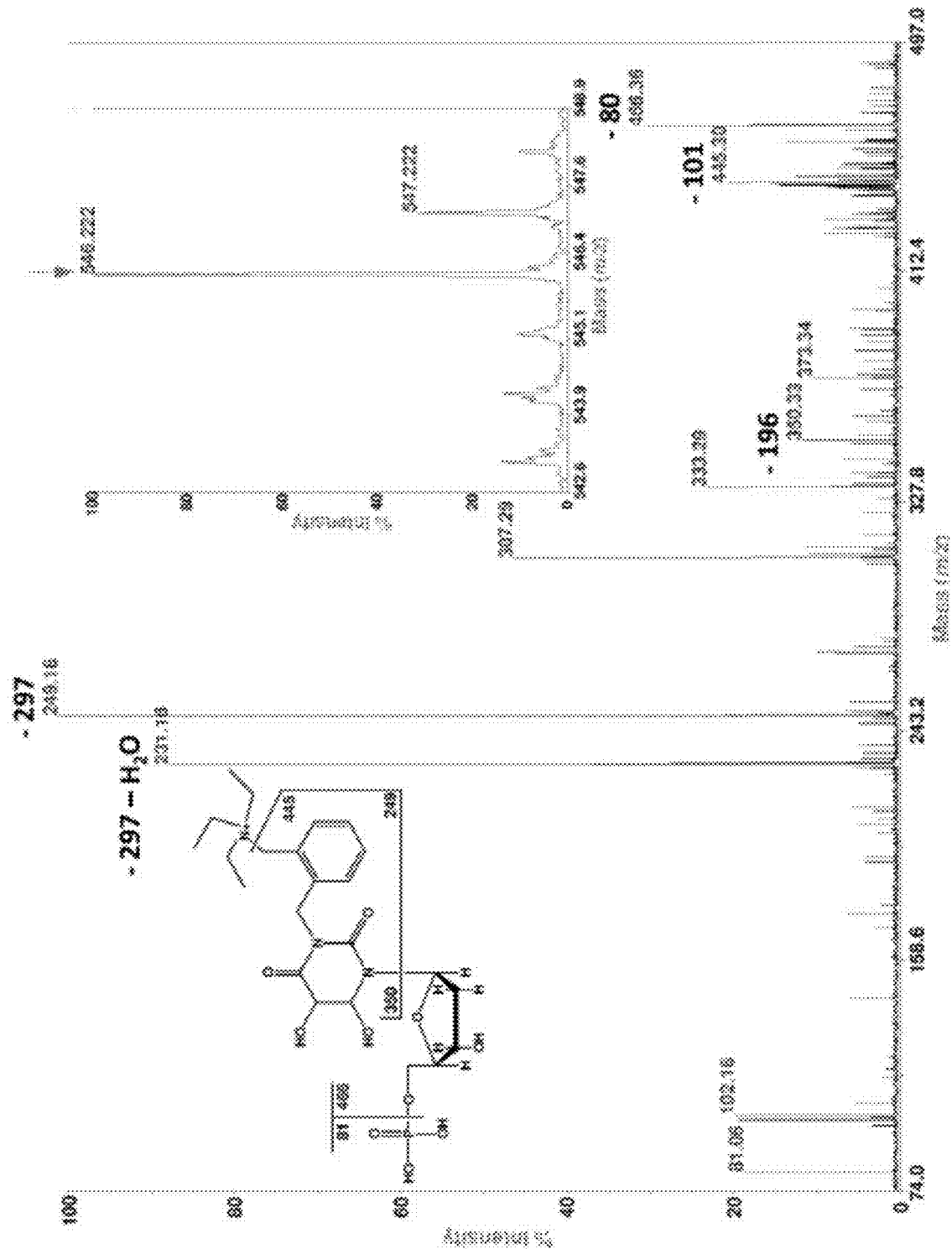
FIG. 4: MALDI-TOF-MS spectrum (inset), and MALDI-TOF/TOF-MS spectrum (main frame), of CAX-glycol-dUMP.

In FIG. 4 is shown the detection of CAX-dUMP-glycol by MALDI-TOF-MS at 546 Da in the inset, along with an [M+H−neutral fragment]+ by MALDI-TOF/TOF-MS in the main frame of the figure. In the latter spectrum, assigned ions are observed at m/z 466, 445, 380, 249, 231 and 81. The minor ion at m/z 100 is from diethylethenylmethylamine (arising from loss of triethylamine via an elimination reaction [23]). Perhaps this adduct forms in DNA by hydrolysis of dCMP to dUMP [35] followed by oxidation of the latter. The data shown are from analysis of human skin DNA.

Example 8. Hydroxymethylcytosine

Figure 5:
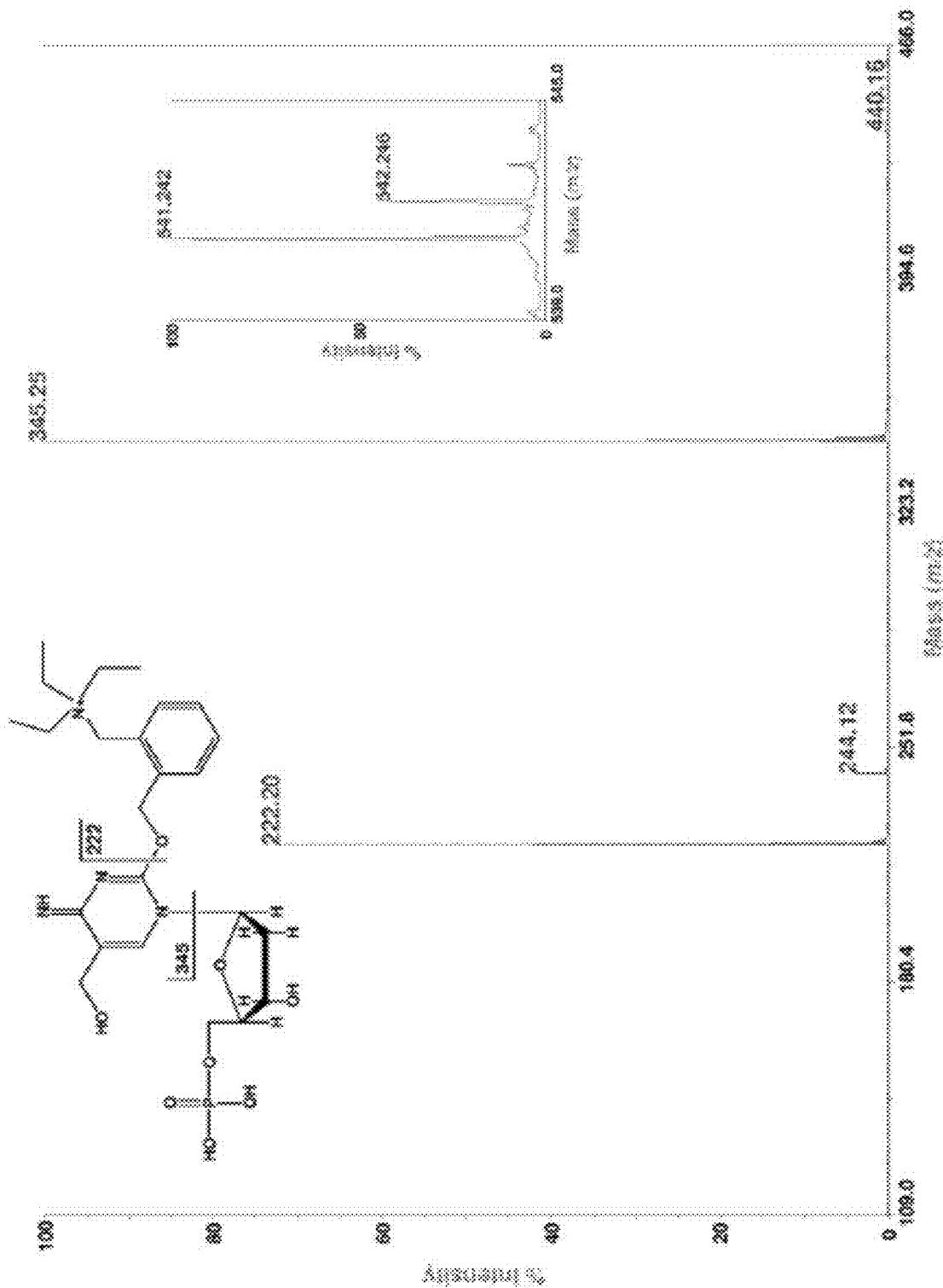
FIG. 5: MALDI-TOF/TOF-MS spectrum of CAX-hydroxymethyl-dCMP from brain DNA. The inset shows the corresponding MALDI-TOF-MS spectrum.
Figures 6A, 6B:
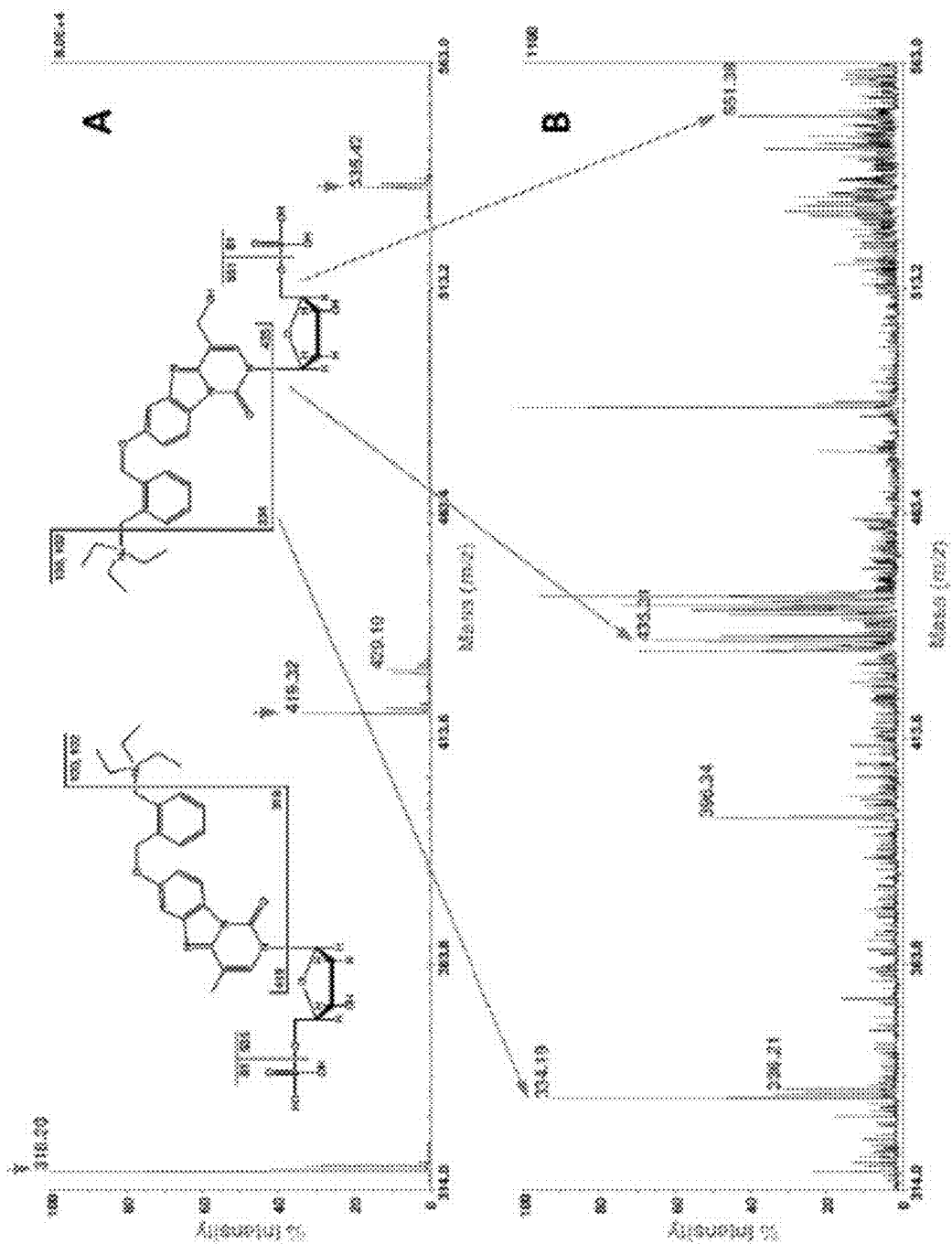
FIG. 6A: MALDI-TOF/TOF-MS spectra of CAX-BQmdCMP.
FIG. 6B: MALDI-TOF/TOF-MS spectra of CAX-BQhmdCMP.
Figure 17:
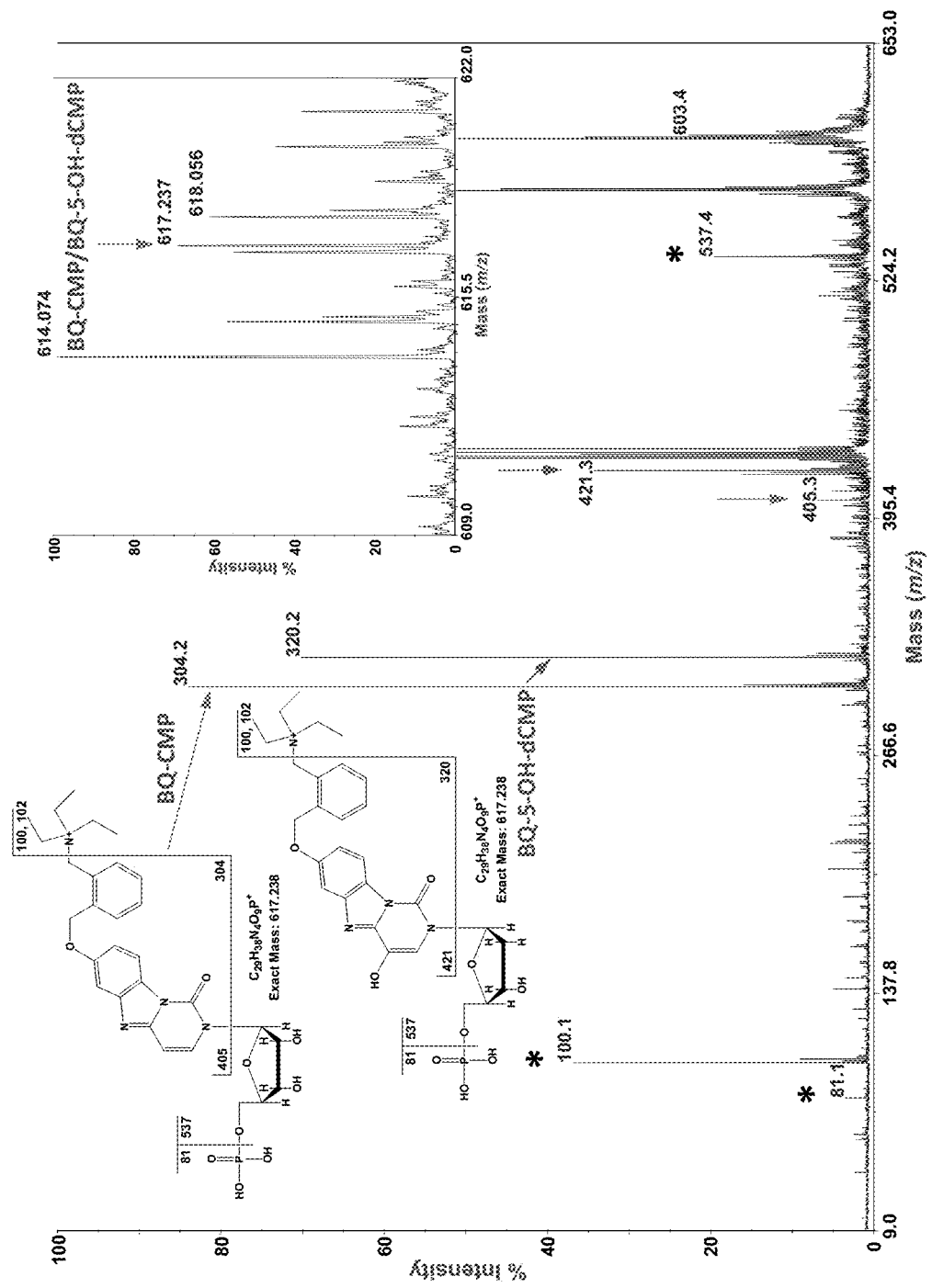
FIG. 17: LC-MALDI-TOF/TOF-MS spectrum of CAX-BQ-5-hydroxy-dCMP from the precursor ion at m/z 617. This data provides an example of RNA contamination identified by LC-MALDI-TOF/TOF-MS. CAX-BQ-CMP and CAX-BQ-5-hydroxy-dCMP [28] share the same mass of 617.238 Da, but are distinguished by MS2, as seen, forming corresponding product ions at m/z 304.2 and 320.2, respectively. Commercial calf thymus DNA always (in our experience) contains some RNA, so it is not surprising to detect BQ-CMP from the BQ-treated calf thymus DNA. The LC-MALDI-TOF/TOF-MS spectrum shows characteristic M-212 (loss of ribose phosphate) and M-313 (loss of ribose phosphate and triethylamine) product ions, as indicated by the red arrows. The inset shows the precursor ion at 617 Da.

The level of hmdCMP in some tissues is relatively high [36]. The inset in FIG. 5 shows the detection of CAX-hmdCMP from brain DNA by MALDI-TOF-MS. The corresponding MS2 spectrum in the main frame shows a product ion at 222 Da. This indicates that the tagging is on oxygen, but which oxygen is unknown. When CAX-dCMP and CAX-mdCMP are selected for MS2 analysis, no product ion at m/z 222 can be observed Example 9. Benzoquinone (BQ) Adducts of Cytosine and Hydroxymethylcytosine The detection of BQ-dCMP in a BQ-treated DNA sample which was estimated to contain 1 residue of this adduct in $10^5$ nucleotides was previously reported [28]. Testing this same DNA by CAX-Prelabeling with LC-MALDI-TOF/TOF MS also reveals this adduct (FIG. 17). Also detected now are corresponding BQ-methyl-dCMP (FIG. 6A) and BQ-hydroxymethyl-dCMP (FIG. 6B) as CAX derivatives. The latter adduct has not been reported before. mdCMP is about 4% of dCMP in the DNA that we tested. If we arbitrarily assume that BQ-hydroxymethyl-dCMP is about 1% of BQ-methyl-dCMP, then we have detected about 4 BQ-hmdCMP in $10^9$ nucleotides by CAX-Prelabeling at S/N ~30 (FIG. 6B). Peak assignments are shown in this figure.

Example 10. Hydroxyethyl-Guanine

We reacted calf thymus DNA with 1-(2-chloroethyl)-3-cyclohexyl-1-nitrosourea (Lomustine [24]) to form hydroxyethyl adducts, and subjected it to CAX-Prelabeling with detection by LC-MALDI-TOF/TOF-MS. This resulted in four chromatographic peaks from four isomers of CAX-labeled hydroxyethyl guanine adducts at retention indices (spot numbers on the MALDI plate, where the central spot for a LC peak is reported) of 42 (C), 44 (A), 55 (D), and 58 (B), each having a precursor ion at 595 Da. The corresponding MS2 spectra for each of these spots is shown in FIG. 7.

The tentative structures shown in FIG. 7 are discussed below based on the fragmentation patterns. The compounds are named according to the subparts of the figure: 7A, 7B, 7C, 7D. Compound 7A is assumed to be CAX-N7-hydroxyethyl-dGMP, having a net charge of +1 as illustrated. Cleavage of the glycolytic bond in this compound is favored in TOF/TOF, we assume, by the positive charge on N7, leading to the major product ion, M-196 (m/z 399). Loss of phosphate is minimal, forming m/z 515, probably because this loss is hindered by the nearby positive charge on the nucleobase. An MM2 energy minimizing calculation predicts a negatively charged oxygen of the phosphate group close to the positively charged N7 position (shown in FIG. 8). In compound 7B by steric effect mainly, the hydroxyethyl moiety is proposed to be on N1, the CAX moiety on N2, and the phosphate is assumed to be neutral, in agreement with the observed fragments and the proposed fragmentation pathway. The observation of m/z at 355 (CAX-G) and 254 (CAX-G-101) in FIGS. 7C and 7D, respectively, instead of the ions at m/z 399 and 298 shown for compounds 7A and 7B, indicates that the hydroxyethyl group is on the phosphate in compounds 7C and 7D. This is further supported by the proposed fragmentation patterns. Charge repulsion may explain the relatively higher intensity of m/z 494 in 7C than in 7D (MM2 calculation, as shown in FIG. 8 and FIG. 13, predicts 7C and 7A to have a similar configuration, and likewise 7D and 7B). The relative chromatographic retention times also are consistent with these assignments: 7A elutes 3.5 min earlier than 7B, and 7C elutes 3.25 min earlier than 7D. Cations, being more polar, should elute earlier than the corresponding zwitterions from a C18 column.

Example 11. Apurinic/Apyrimidinic Sites in DNA

Figure 9:
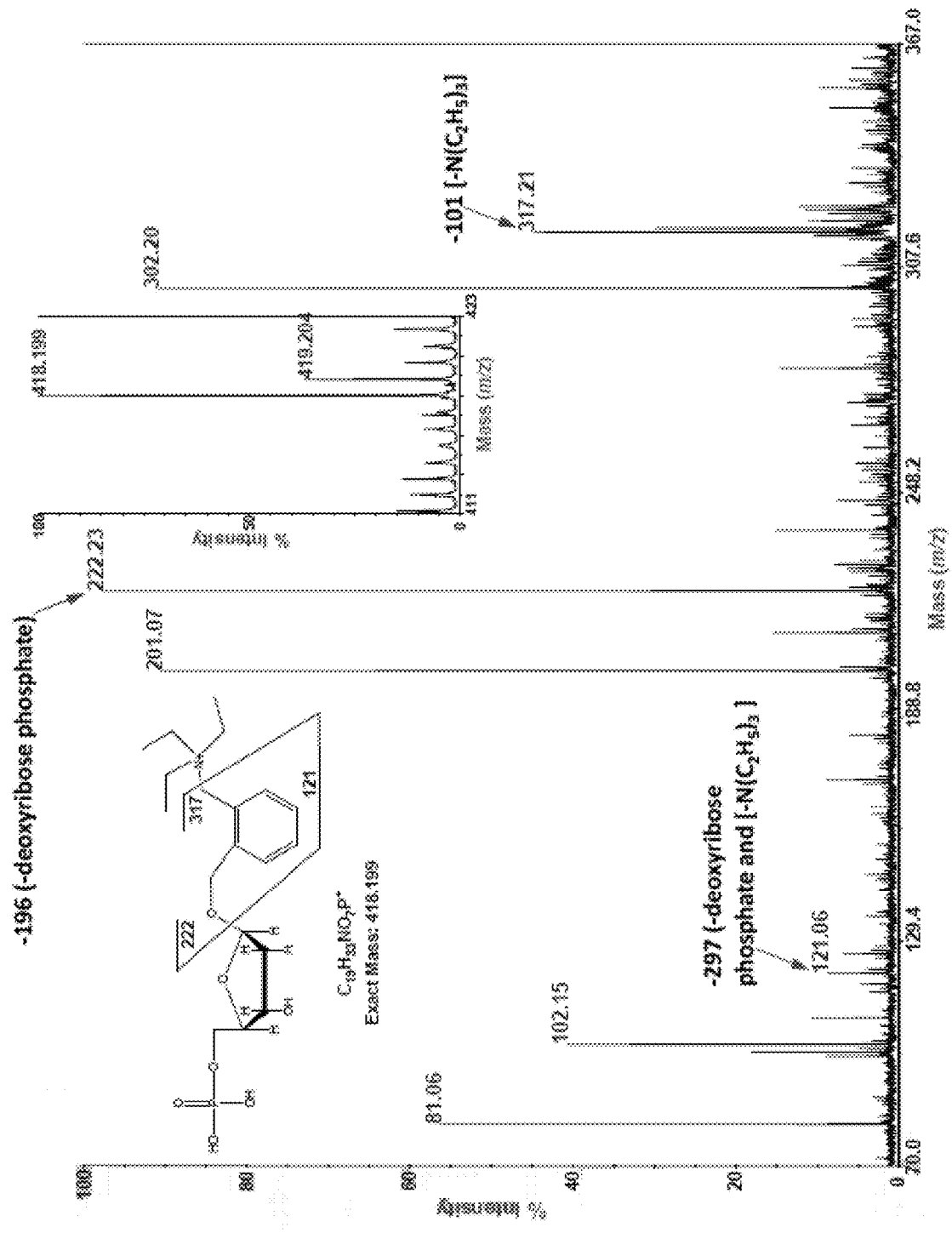
FIG. 9: Detection of Apurinic/Apyrimidinic (AP) sites in human skin DNA by CAX-Prelabeling with detection by LC-MALDI-TOF-MS (inset) and LC-MALDI-TOF/TOF-MS (main frame).

FIG. 9 shows the detection of Apurinic/Apyrimidinic (AP) sites in human skin DNA by CAX-Prelabeling with detection by LC-MALDI-TOF-MS and LC-MALDI-TOF/TOF-MS. In the inset is shown the mass spectrum of an LC peak recorded from one of the three MALDI spots observed to contain this compound at about 14.7 min when m/z 418 is monitored. This relatively low retention time corresponds to a very polar adduct; indeed the peak elutes earlier than that of CAX-dCMP (about 16.9 min). As seen, the detected mass (418.199) fully agrees with that of the assignment (418.199). In the main frame of the figure, the fragmentation data by LC-MALDI-TOF/TOF-MS confirms the structure shown (aside from the stereochemistry of the glycosidic bond), based on peaks at m/z 121, 222, and 317. The abundance of this peak at m/z 418 for AP is about two-fold higher than that from fC or hmC, but about two-fold lower than from fapy A. AP sites also have been detected in other studies by another form of mass tag prelabeling. For example, Chen et al [37] used a pyridinyl-hydroxylamine mass tag reagent to label such sites in their ring-opened aldehyde form in DNA, yielding an oxime for subsequent detection by LC-MS.

Example 12. Benzo[a]Pyrene-Guanine

Figure 10B:
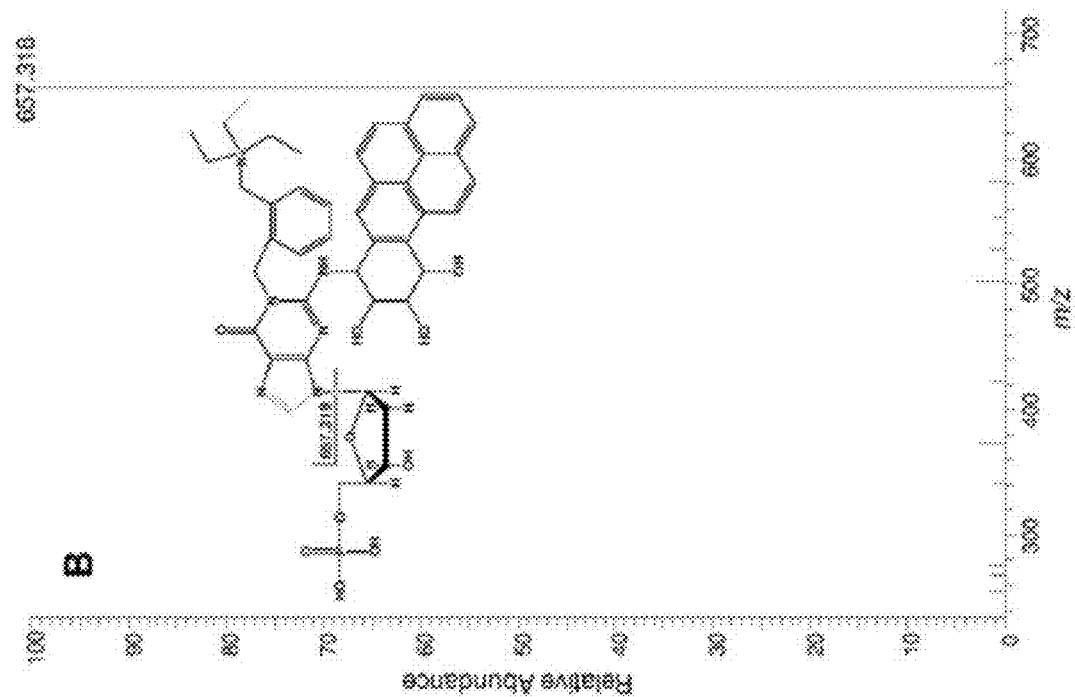
FIG. 10B: A. MS2 spectrum obtained at the maximum of the peak at 21.78 min.
Figure 10A:
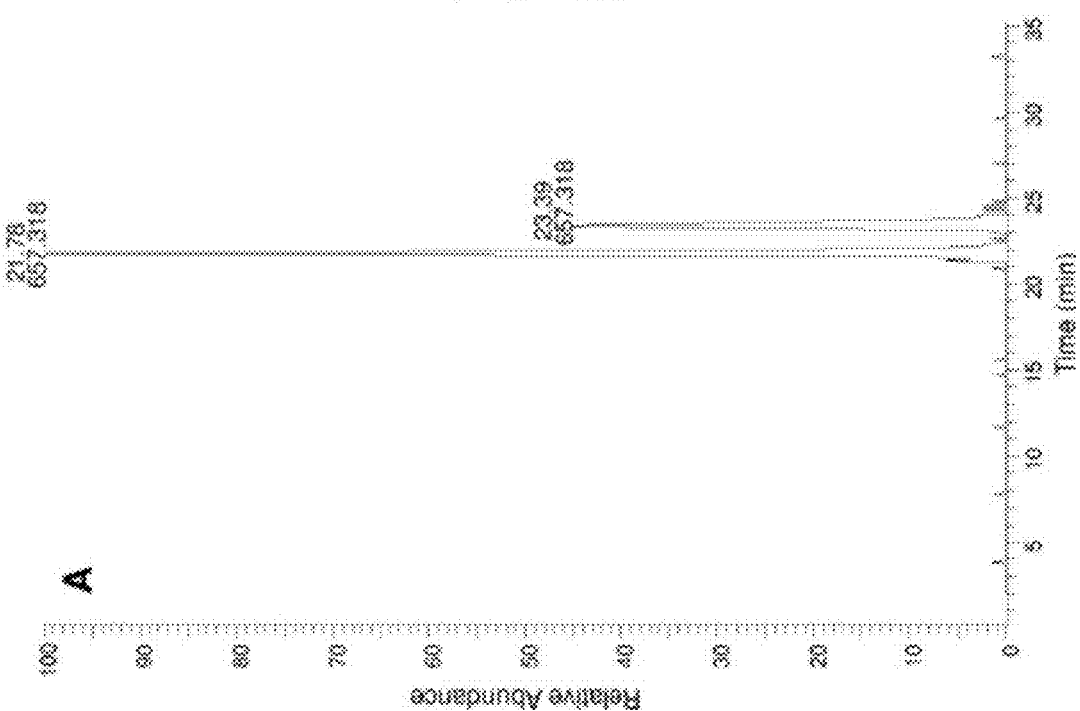
FIG. 10A: A. SIM LC-LTQ Orbitrap chromatogram from CAX-Prelabeling applied to DNA treated with B[a]P-diolepoxide, monitoring the product ion at 657.319±0.05 Da derived from the precursor ion at m/z 853.3±0.5 Da.

A sample of DNA containing benzo[a]pyrene guanine adducts, prepared as described [27], was subjected to CAX-Prelabeling. The CAX-labeled nucleotides derived from 0.5 μg of DNA were injected into an LC-Orbitrap LTQ. Monitoring the product ion (from the precursor ion at 853.3±0.5 Da) at m/z 657.319±0.05 Da, extracted from the Orbitrap MS2 full scan spectra, gave the SIM mass chromatogram shown in FIG. 10A. Two peaks are seen, in agreement with the prior study [27]. The full MS2 mass spectrum for the peak at 21.78 min, obtained at its maximum intensity, is shown in FIG. 10B. A product ion, from loss of deoxyribose phosphate, is seen at m/z 657.318 (accurate mass 657.319). The peak at 23.29 min in FIG. 10A gives the same result.

Example 13. Detection of Additional Adducts

Figure 11:
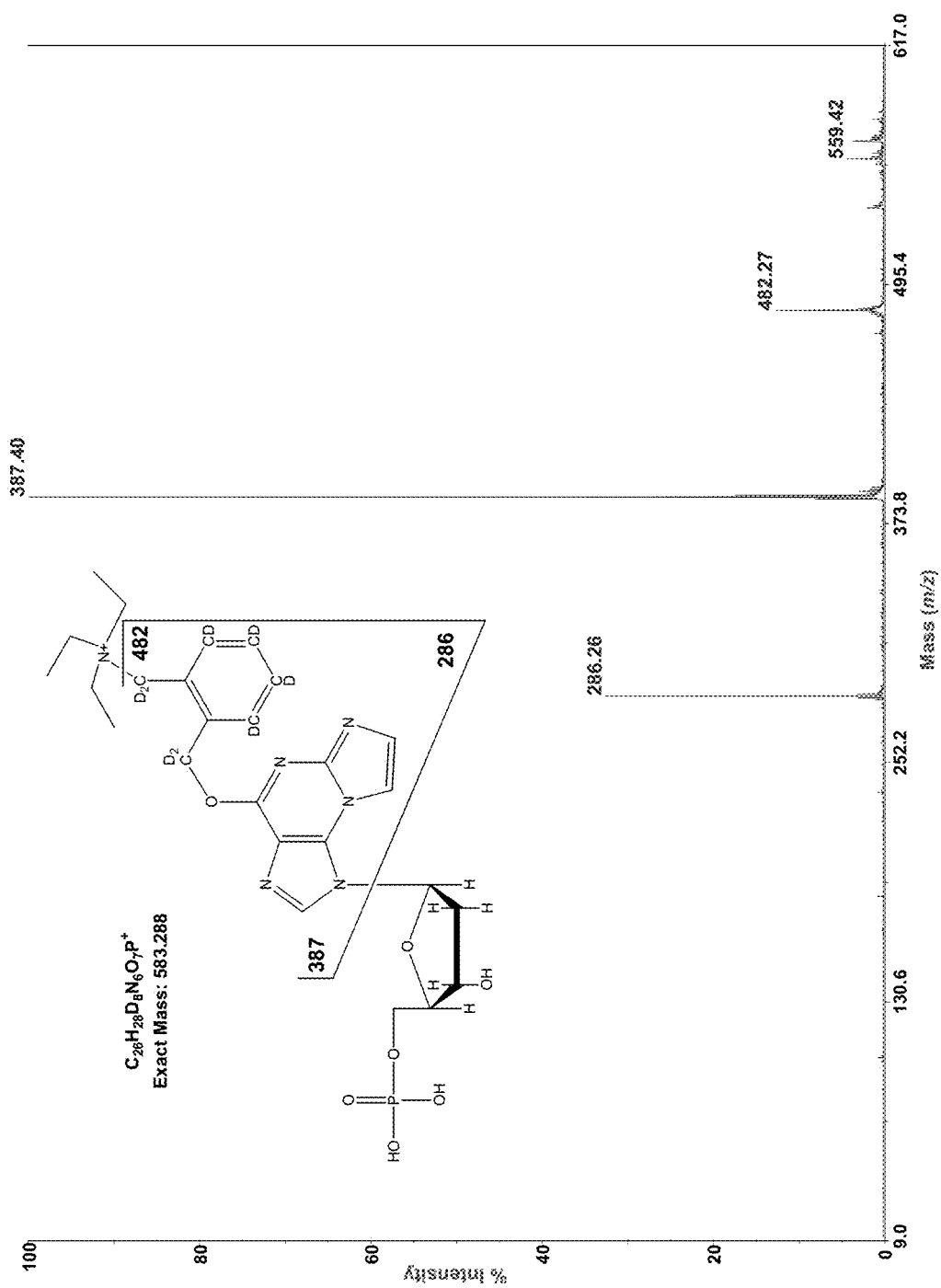
FIG. 11: LC-MALDI-TOF/TOF-MS spectrum of CAX-$d_8$-etheno-dGMP. After chloroacetaldehyde was used to generate etheno adducts in calf thymus DNA as described [25], CAX-Prelabeling with CAX-B-$d_8$ then was done, leading to detection of etheno-dGMP, based on use of LC-MALDI-TOF/TOF-MS.
Figure 12:
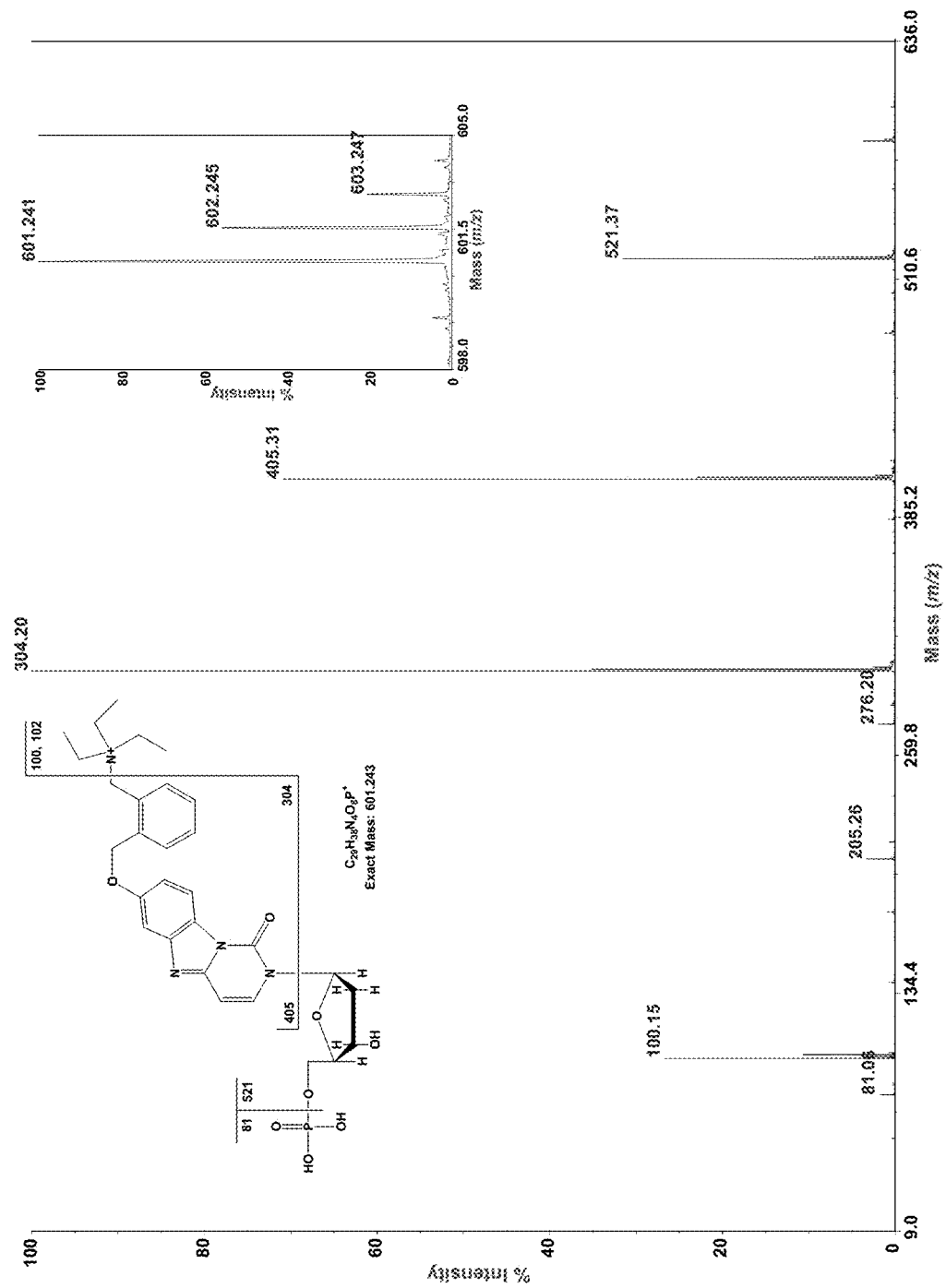
FIG. 12: LC-MALDI-TOF/TOF-MS and LC-MALDI-TOF-MS spectra of CAX-BQ-dCMP, having a mass of 601 Da. This BQ-treated DNA sample previously was estimated to contain 1 BQ adduct of cytosine in $10^5$ nucleotides [28]. Testing this same DNA sample by CAX-Prelabeling with LC-MALDI-TOF-MS reveals this adduct peak at 601 Da as shown in the inset. The main plot shows MS2 data.
Figure 14:
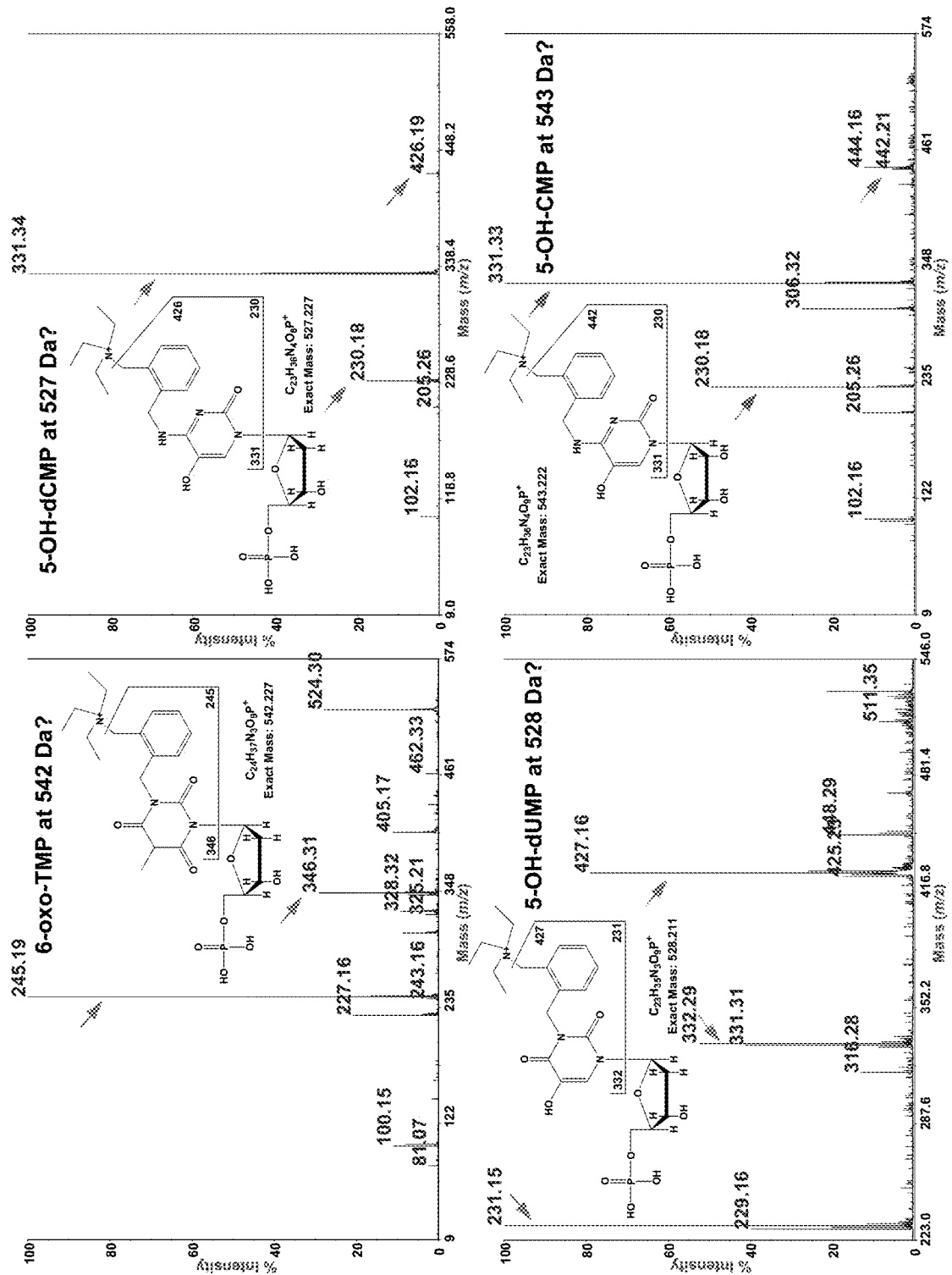
FIG. 14: MALDI-TOF/TOF-MS of CAX-labeled oxidative adducts. Oxidative DNA adducts arising from treatment of DNA with bromoacetic acid. The assignments of the four DNA adducts are tentative [30,35], as indicated. While CAX-5-OH-dCMP and CAX-5-OH-CMP (on the right) differ in mass by the equivalent of 1 atom of oxygen, their product ions at m/z 331 and 230 are identical for each due to loss of phosphate-sugar, and triethylamine plus phosphate-sugar, respectively.
Figure 15:
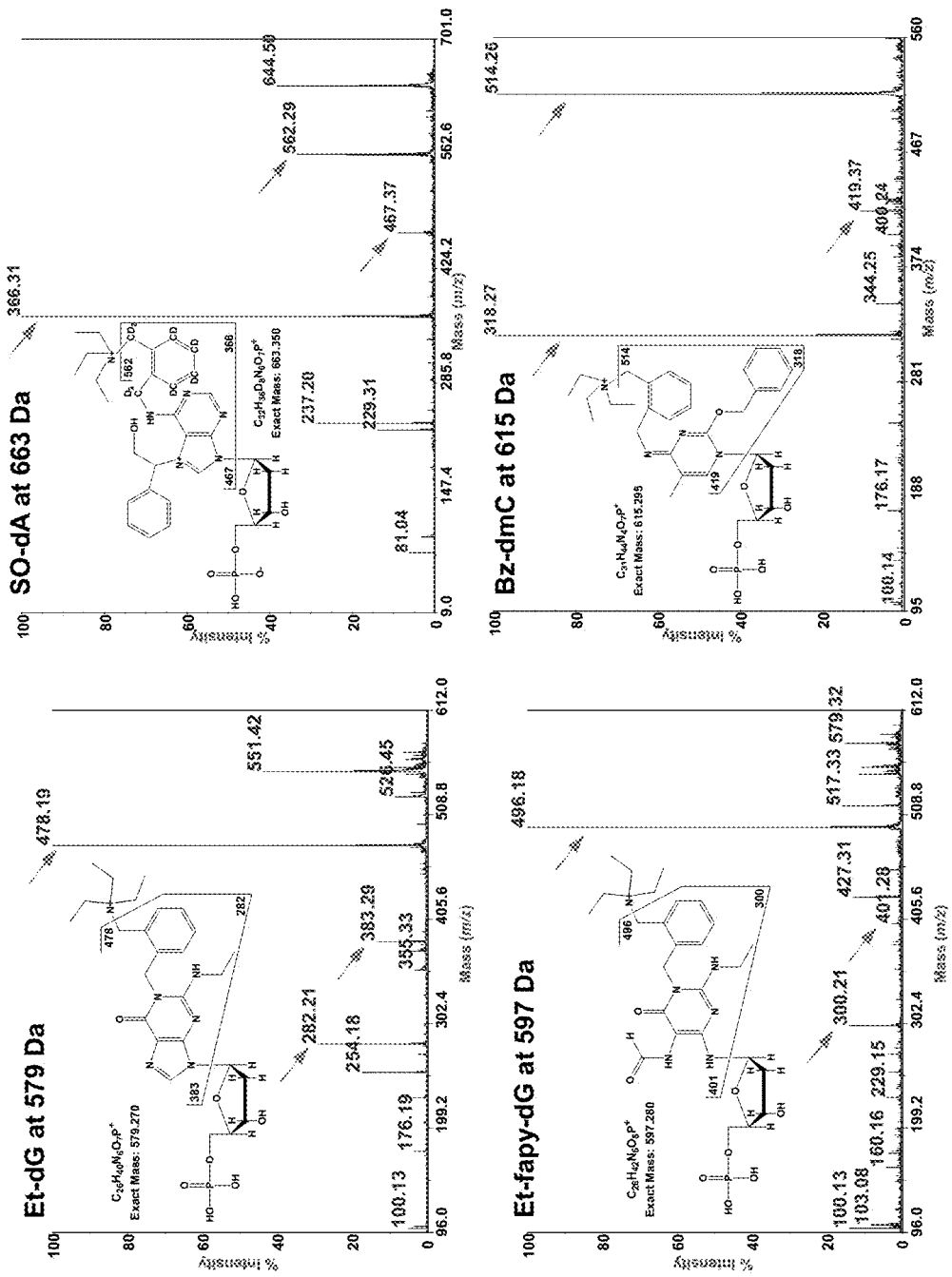
FIG. 15: MALDI-TOF/TOF-MS spectra of four CAX-DNA adducts: ethyl, styrene oxide, ethyl-fapy, and benzyl. In each case the precursor ion is given. The dominating product ions (indicated by the red arrows), as usual, are M-101 (loss of triethylamine), and M-196 (loss of deoxyribose phosphate) or M-297 (loss of triethylamine and deoxyribose phosphate), depending on the structure of the modified base and its site that is labeled by CAX. M-196 and M-297 are both deoxynucleotide specific features.
Figure 16:
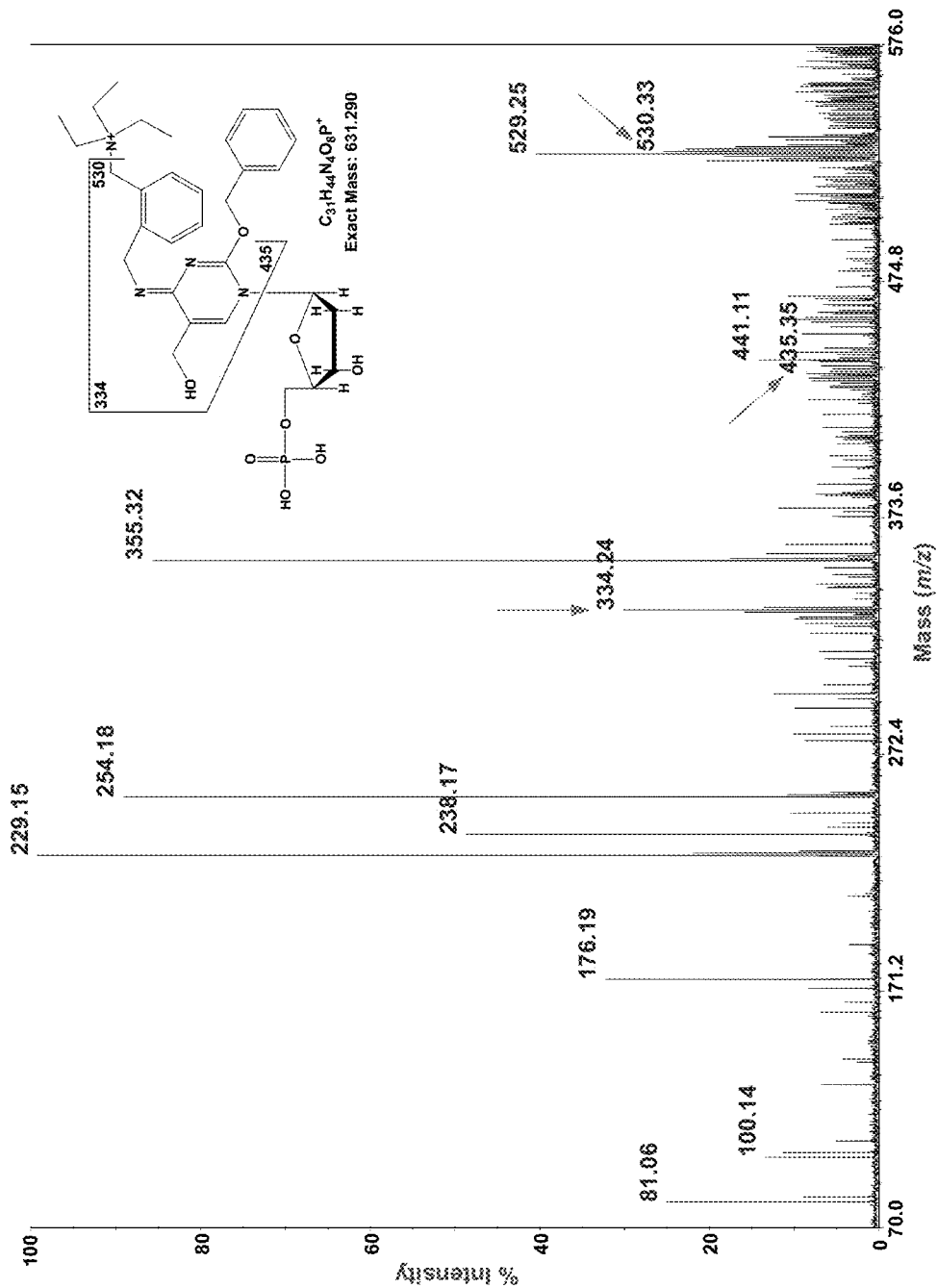
FIG. 16: LC-MALDI-TOF/TOF-MS spectrum of CAX-Bz-hmdCMP from the precursor ion at m/z 631. Benzylation of DNA was done as described [24]. The peak at m/z 334 arises from loss of 297 (triethylamine neutral plus phosphate deoxyribose).

FIGS. 11, 12, and 13 show the detection of other DNA adducts that were formed by conducting reactions of chemicals with calf thymus DNA in the test tube, along with some RNA species arising from the fact that RNA almost always is a contaminant of such DNA. The tentative detection of four oxidative adducts is shown in FIG. 14: 6-oxo-TMP, 5-OH-dCMP, 5-OH-dUMP, and 5-OH-CMP. The detection of ethyl-dGMP, styrene oxide-dAMP, ethyl-fapy-dGMP, and benzyl-methyl-dCMP adducts is shown in FIG. 15. FIG. 16 presents the detection of benzylhydroxymethyl-dCMP. In FIG. 17 is shown the detection of benzoquinone-CMP and benzoquinone-5-hydroxy-dCMP from DNA treated with benzoquinone.

Example 14. Detection of DNA Adducts in a Nucleoside Form Via CAX-B Prelabeling/Neutral Thermal Hydrolysis/MS CAX-B in 50% ACN (20 mg/mL), with $Et_3N$ (30 µL/mL), is mixed 1:2 (v/v) with a solution of DNA (100 µL at ~1 mg/mL in water). After 2 h at 45° C., the reaction mixture is adjusted with phosphate buffer, 50 mM, pH 7.0, and kept in a sealed tube for 72 h at 37° C. The tube is then heated at 95° C. for 4 h. After passing through an OASIS MAX solid phase extraction cartridge, and washing with 2×100 µL of 50% ACN, the combined filtrates are evaporated, re-dissolved in 20 µL of 6:94, v/v, ACN:water, and 5 µL is injected into one of the above mass spectrometer systems.

Example 15. Other Adducts and Mass Spectrometer Systems

This invention can be practiced with other quaternary amine reagents, such as those having benzyl tosylate, aniline, benzaldehyde, active ester, epoxide, isothiocyanate, hydrazide, or an oxyamino reactive group. This invention can be practiced with other mass spectrometry systems such as those having a component selected from ion mobility or ion trap.

Discussion

Disclosed herein is a CAX-Pre-labeling method for DNA adductomics. This labeling technique is done with a CAX mass tag rather than a radiolabel prior to enzymatic digestion of the DNA to nucleotides. Also, the detection in this method is done by mass spectrometry. CAX-Prelabeling is presented as a complementary technique to current practice for DNA adductomics, especially because it encompasses a diversity of polar DNA adducts for the first time in a single procedure under a single set of conditions throughout.

The methods involves directly reacting intact, ds-DNA under warm conditions with an alkylating mass tag followed by mass spectrometry. The adducted nucleobases tend to locally disrupt DNA structure (forming a "DNA bubble") in a way that increases exposure of their nucleophilic (including active hydrogen) sites. In contrast, canonical nucleobases in native ds-DNA regions resist such alkylation by failing to bubble.

More specifically, a diversity of DNA adducts were detected by the following steps: (1) react DNA at 45° C. for 2 h under aqueous conditions with CAX-B (an alkylating quaternary amine mass tag that labels active hydrogen sites) in the presence of triethylamine; (2) remove residual reagents by precipitating and washing the DNA; (3) digest the DNA enzymatically to nucleotides and remove unlabeled nucleotides by nonpolar solid phase extraction; and (4) detect CAX labeled adducted nucleotides by LC-MS or MALDI-TOF/TOF-MS.

Examples of the 38 DNA adducts detected (based on accurate mass and fragmentation data) in this way are as follows: 8-oxo-dGMP, ethyl-dGMP, benzo[a]pyrene-dGMP, and, for the first time, benzoquinone-hydroxymethyl-dCMP. Sensitivity is only defined in a preliminary way, namely the latter adduct seems to be detected at a level of about 4 adducts in 109 nucleotides (S/N ~30). This is the first DNA adductomics method that simultaneously detects adducts ranging from small polars to large nonpolars in a specific way.

Five limitations of CAX-Prelabeling assay for DNA adducts are immediately apparent. (1) Some DNA adducts stabilize local structure of ds-DNA [31], and thereby are anticipated to resist labeling. (2) Normal nucleotides especially in the bubbled DNA regions are expected to be labeled as well, increasing background signals. This is indicated by the scheme shown in FIG. 1. (3) A given DNA adduct may have multiple active hydrogens (whether on the base or adducted chemical) that can undergo labeling, decreasing the signal by dividing it over multiple chromatographic peaks. (4) CAX-labeling of a DNA adduct might interfere with subsequent enzymatic digestion of the DNA to monomers for detection by mass spectrometry. (5) The yield of the labeling step can be adduct dependent, compromising sensitivity and absolute quantitation.

These disadvantages potentially can be mitigated by the following, corresponding considerations: (1) Adducts that stabilize ds-DNA structure probably are rare [31]. Indeed, nucleotide excision repair, which primarily recognizes DNA bubbles, recognizes a great diversity of DNA adducts [32-34]. Further, nonphysiological conditions might increase exposure of such adducts. (2) Peaks from normal nucleotides provide calibration and carrier contributions. (3) Multiple peaks from an adduct can facilitate its characterization; further, each peak should come from a mono-labeled adduct due to charge repulsion (the positive charge deposited on the adduct by the first CAX moiety tends to repel other CAX-B molecules). (4) Potentially an adduct can be detected in a CAX-labeled dinucleotide or trinucleotide form; further a diversity of nucleases is available to increase the opportunity to form a CAX-mononucleotide from a given adduct (or in planned future studies, from a CAX-mononucleoside). (5) The high sensitivity of the CAX tag can enable adequate sensitivity even when the labeling yield is low, and relative quantitation, which is valuable in DNA adductomics, is provided.

There are also other advantages of the CAX-prelabeling for DNA adducts, in addition to those cited above. (1) It is a DNA adductomics method that simultaneously detects polar and nonpolar adducts, whereas other techniques only detect either polar or nonpolar adducts at once. (2) Residual mass tag can be removed easily from the CAX-reacted DNA sample by membrane filtration or DNA precipitation (which helps to make the method practical). (3) When the labeled DNA is digested to nucleotides, CAX-labeled adducts will be zwitterions (unless the adducted chemical itself carries a charge), in contrast to the anionic canonical nucleotides, helping to achieve broad enrichment of adducts prior to detection, and further helping to make the assay practical. (4) Artifactual production of DNA adducts after the labeling step is much less of a concern, since it will tend to affect only a tiny fraction of the CAX-labeled adducts vs. artifactual production on a larger scale from the overall DNA. This is important for detection of oxidative DNA adducts, which tend to form artifactually. (5) Triethylamine is an antioxidant, further reducing the likelihood of artifactual oxidative DNA adducts. (6) CAX-labeling up-shifts the masses of DNA adducts by about 200 Da, reducing interferences from low-mass background ions in the mass spectrometer. (7) When CAX-labeled nucleotides are subjected to collision-induced dissociation (CID) in the mass spectrometer, the following two types of analyte-specific product ions tend to form: M-196 from loss of deoxyribose phosphate, and M-297 from combined loss of triethylamine and deoxyribose phosphate. These ions distinguish DNA adducts from ribonucleotide species (a feature similarly shared with the sugar-loss method). (8) Not only the simple steps in the method, but also the use of a single set of conditions throughout for at least many adducts additionally helps to make the method practical. (9) The method is anticipated to detect phosphate adducts, at least when digestion is extended to nucleosides [17], as long as one of the bases in the dinucleoside product provides an active hydrogen for CAX-labeling. (10) There is a good opportunity to shift the mass of a detected adduct to deal with noise as needed, since CAX-B-d8 is readily available (it is employed here in FIG. 11). (11) The method is anticipated to detect adducts that resist neutral loss of sugar, since a neutral loss moiety is built into the CAX mass tag. (12) CAX-B is easily synthesized in a single step from inexpensive, common reagents [23]. (13) CAX has a moderate nonpolar structure, enough to increase the retention time of polar analytes into a less noisy region of a reversed-phase LC separation while retaining resolution. For example, as presented below, four isomers of CAX-labeled hydroxyethyl-dGMP are resolved in this way. (14) CAX-labeled adducts can be detected by both MALDI-MS and ESI-MS. (15) Radiolabeling is nonspecific unlike the disclosed method, and (16) allows for a sample of blood to provide a comprehensive DNA adductomics test.

REFERENCES CITED

1. Tretyakova N, Villalta P W, Kotapati S. Mass spectrometry of structurally modified DNA. *Chem. Rev.* 2013; 113: 2395-2436.
2. Geacintov N E, Broyde S. Ed. The Chemical Biology of DNA Damage. Wiley—VCH Verlag GmbH & Co. KGaA, Weinheim. 2010.
3. Balbo S, Turesky R J, Villalta, P W. DNA Adductomics. *Chem. Res. Toxicol.* 2014; 27: 356-366.
4. Pottenger L H, Andrews L S, Bachman A N, Boogaard P J, Cadet J, Embry M R, Farmer P B, Himmelstein M W, Jarabek A M, Martin E A, Mauthe R J, Persaud R, Preston R J, Schoeny R, Skare J, Swenberg J A, Williams G M, Zeiger E, Zhang F, Kim, J H. An organizational approach for the assessment of DNA adduct data in risk assessment: case studies for aflatoxin B1, tamoxifen and vinyl chloride. *Crit. Rev. Toxicol.* 2014; 44: 348-391.
5. Liu S, Wang Y. Mass spectrometry for the assessment of the occurrence and biological consequences of the DNA adducts. *Chem. Soc. Rev.* 2015; 44: 7829-7854.
6. Stornetta A, Zimmermann M, Cimino G D, Henderson P T, Sturla S J. DNA Adducts from Anticancer Drugs as Candidate Predictive Markers for Precision Medicine. *Chem. Res. Toxicol.* 2017; 30: 388-409.
7. Sturla S J. DNA Adduct Profiles: Chemical Approaches to Addressing the Biological Impact of DNA Damage from Small Molecules. *Curr. Opin. Chem. Biol.* 2007; 11(3): 293-299.
8. Villalta P W, Balbo S. The Future of DNA Adductomic Analysis. *Int. J. Mol. Sci.* 2017; 18(9): 1870.
9. Yun B H, Guo J, Bellarmi M, Turesky R J. DNA Adducts: Formation, biological effects, and new specimens for mass spectrometric measurements in humans. *Mass Spectrom. Rev.* 2020; 39: 55-82.
10. Yun B H, Rosenquist T A, Nikolić J, Dragičević D, Tomić K, Jelaković B, Dickman K G, Grollman A P, Turesky R J. Human Formalin-Fixed Paraffin—Embedded Tissues: An Untapped Specimen for Biomonitoring of Carcinogen DNA Adducts by Mass Spectrometry. *Anal. Chem.* 2013; 85: 4251-4258.
11. Yun B H, Rosenquist T A, Sidorenko V, Iden C R, Chen C H, Pu Y S, Bonala R, Johnson F, Dickman K G, Grollman A P, Turesky R J. Biomonitoring of aristolactam-DNA adducts in human tissues using ultra-performance liquid chromatography/iron-trap mass spectrometry. *Chem. Res. Toxicol.* 2012; 25: 1119-1131.
12. Gu D, Turesky R J, Tao Y, Langouët S A, Nauwelaërs G C, Yuan J M, Yee D, Yu M C. DNA adducts of 2-amino-1-methyl-6-phenylimidazo[4,5-b]pyridine and 4-aminobiphenyl are infrequently detected in human mammary tissue by liquid chromatography/tandem mass spectrometry. *Carcinogenesis* 2012; 33: 124-130.
13. Bessette E E, Spivack S D, Goodenough A K, Wang T, Pinto S, Kadlubar F F, Turesky RJ. Identification of carcinogen DNA adducts in human saliva by linear quadrupole ion trap/multistage tandem mass spectrometry. *Chem. Res. Toxicol.* 2010; 23: 1234-1244.
14. Goodenough A K, Schut H A J, Turesky R J. Novel LC-ESI-MS/MSn method for the characterization and quantification of 2'-deoxyguanosine adducts of the dietary carcinogen 2-amino-1-methyl-6phenylimidazo[4,5-b]pyridine by 2-D linear quadrupole ion trap mass spectrometry. *Chem. Res. Toxicol.* 2007; 20: 263-276.
15. Monien B H, Schumacher F, Herrmann K, Glatt H, Turesky R J, Chesne C. Simultaneous Detection of Multiple DNA Adducts in Human Lung Samples by Isotope-Dilution UPLC-MS/MS. *Anal. Chem.* 2014; 87: 641-648.
16. Singh R, Teichert F, Seidel A, Roach J, Cordell R, Cheng M K, Frank H, Steward W P, Manson M M, Farmer P B. Development of a targeted adductomics method for the determination of polycyclic aromatic hydrocarbon DNA adducts using online column-switching liquid chromatography/tandem mass spectrometry. *Rapid Commun. Mass Spectrom.* 2010; 24: 2329-2340.
17. Ma B, Zarth A T, Carlson E S, Villalta P W, Upadhyaya P, Stepanov I, Hecht S S. Identification of more than 100 structurally unique DNA-phosphate adducts formed during rat lung carcinogenesis by the tobacco-specific nitrosamine 4-(methylnitrosamino)-1-(3-pyridyl)-1-butanone. *Carcinogenesis* 2018; 39: 232-241.
18. Balbo S, Meng L, Bliss R L, Jensen J A, Hatsukami D K, Hecht S S. Time course of DNA adduct formation in peripheral blood granulocytes and lymphocytes after drinking alcohol. *Mutagenesis* 2012; 27: 485-490.
19. Pang B, Zhou X, Yu H, Dong M, Taghizadeh K, Wishnok J S, Tannenbaum S R, Dedon P C. Lipid peroxidation dominates the chemistry of DNA adduct formation in a mouse model of inflammation. *Carcinogenesis* 2007; 28: 1807-1813.
20. Taghizadeh K, McFaline J L, Pang B, Sullivan M, Dong M, Plummer E, Deon P C. Quantification of DNA damage products resulting from deamination, oxidation and reaction with products of lipid peroxidation by liquid chromatography isotope dilution tandem mass spectrometry. *Nat. Protoc.* 2008; 3(8):1287-1298.
21. Hemeryck L Y, Decloedt A I, Bussche J V, Geboes K P, Vanhaecke L. High resolution mass spectrometry based profiling of diet-related deoxyribonucleic acid adducts. *Anal. Chim. Acta* 2015; 892: 123-131.
22. Randerath K, Randerath E. 32P-Postlabeling methods for DNA adduct detection: overview and critical evaluation. *Drug Metab. Rev.* 1984; 2 6:67-85.
23. Wang P G, Zhang Q, Yao Y Y, Giese R W. Cationic xylene tag for increasing sensitivity in mass spectrometry. *J. Am. Soc. Mass Spectrom.* 2015; 26: 1713-1721.

24. Moschel R C, Hudgins W R, Dipple A. Selectivity in nucleoside alkylation and aralkylation in relation to chemical carcinogenesis. *J. Org. Chem.* 1979; 44: 3324-3328.
25. Sattsangi P D, Leonard N J, Frihart CR. 1,N2-Ethenoguanine and N2,3-ethenoguanine. Synthesis and comparison of the electronic spectral properties of these linear and angular triheterocycles related to the Y bases. *J. Org. Chem.* 1977; 42: 3292-3296.
26. Schrader W, Linscheid M. Styrene oxide DNA adducts: in vitro reaction and sensitive detection of modified oligonucleotides using capillary zone electrophoresis interfaced to electrospray mass spectrometry. *Toxicol.* 1997; 71: 588-595
27. Straub K M, Meehan T, Burlingame A L, Calvin M. Identification of the major adducts formed by reaction of benzo(a)pyrene diol epoxide with DNA in vitro. *Proc. Natl. Acad. Sci. U.S.A.* 1977; 74: 5285-5289.
28. Wang P G, Gao J, Li G, Shimelis O, Giese R W. Nontargeted Analysis of DNA Adducts by Mass-Tag MS: Reaction of P-Benzoquinone with DNA. *Chem. Res. Toxicol.* 2012; 25: 2737-2743
29. Evrony G D, Cai X Y, Lee E, Hills L B, Elhosary P C, Lehmann H S, Parker J J, Atabay K D, Gilmore E C, Poduri A, Park P J, Walsh C A. Single-neuron Sequencing Analysis of L1 Retrotransposition and Somatic Mutation in the Human Brain. *Cell* 2012; 151: 483-96.
30. Wang P G, Fisher D, Rao A, Giese R W. Nontargeted nucleotide analysis based on benzoylhistamine labeling-MALDI-TOF/TOF-MS: discovery of putative 6-oxo-thymine in DNA. *Anal. Chem.* 2012; 84: 3811-3819.
31. Geacintov N E, Broyde S. Repair-Resistant DNA Lesions. *Chem. Res. Toxicol.* 2017; 30: 1517-1548.
32. Reardon J T, Sancar A. Nucleotide Excision Repair. *Prog. Nucleic Acid Res. Mol. Biol.* 2005; 79: 183-235.
33. Kisker C, Kuper J, Van Houten B. Prokaryotic nucleotide excision repair. *Cold Spring Harb Perspect Biol* 2013; 5: a012591.
34. Choi J H, Kim S Y, Kim S K, Kemp M G, Sancar A. An Integrated Approach for Analysis of the DNA Damage Response in Mammalian Cells, *J. Biol. Chem.* 2015; 290: 28812-28821.
35. Kreutzer D A, Essigmann J M. Oxidized, deaminated cytosines are a source of C to T transitions in vivo. *Proc. Natl. Acad. Sci. U.S.A.* 1998; 95: 3578-3582.
36. Kriaucionis S, Heintz N. The Nuclear DNA base 5-hydroxymethylcytosine is present in purkinje neurons and the brain. *Science* 2009; 324: 929-930.
37. Chen H, Yao L, Brown C, Rizzo C J, Turesky R J. Quantitation of Apurinic/Apyrimidinic Sites in Isolated DNA and in Mammalian Tissue with a Reduced Level of Artifacts. *Anal. Chem.* 2019; 91: 7403-7410.

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for detecting the presence of a DNA adduct in DNA, comprising the following steps:
   (1) reacting an adducted nucleotide in the DNA with a labeling precursor L1 to provide an adducted nucleotide labeled with label L, wherein a nucleophilic moiety on the adducted nucleotide reacts with the labeling precursor L1;
   (2) enzymatically digesting the DNA to provide a free adducted nucleotide comprising the label L; and
   (3) detecting the free adducted nucleotide comprising the label L by mass spectrometry,
   wherein the label L comprises a quaternary amine group.

2. The method of claim 1, wherein the adducted nucleotide comprises a nucleobase and an adducted moiety X which is bonded to the nucleobase of the nucleotide.

3. The method of claim 2, wherein the label L is covalently bonded to the nucleobase.

4. The method of claim 2, wherein the label L is covalently bonded to the adducted moiety X.

5. The method of claim 2, wherein the nucleobase is an adenine (A), cytosine (C), methyl-cytosine (MeC), guanine (G), thymine (T), or uracil (U).

6. The method of claim 2, wherein the adducted moiety X is an oxo, alkyl, hydroxyl, hydroxyalkyl, benzyl, or aryl moiety.

7. The method of claim 6, wherein the adducted moiety X is a hydroxymethyl or hydroxyethyl moiety.

8. The method of claim 6, wherein the adducted moiety X is an aryl moiety.

9. The method of claim 8, wherein the adducted moiety X is a benzoquinone moiety or benzopyrene moiety.

10. The method of claim 1, wherein the labeling precursor L1 has the structure:

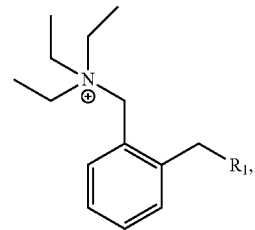

wherein $R_1$ is a leaving group.

11. The method of claim 10, wherein the label L has the following structure:

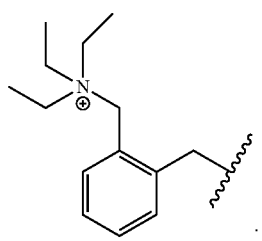 [SMILES: *Cc1ccccc1C[N+](CC)(CC)CC]

12. The method of claim 1, wherein the labeling precursor L1 has the structure:

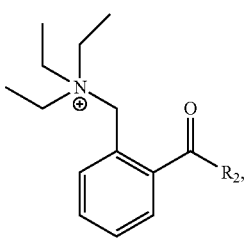

wherein $R_2$ is a leaving group.

13. The method of claim 12, wherein the label L has the following structure:

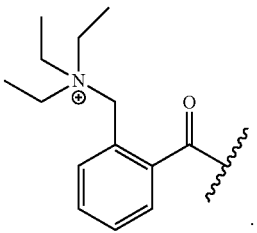 [SMILES: *C(=O)c1ccccc1C[N+](CC)(CC)CC]

14. The method of claim 1, wherein the reaction in step (1) occurs at about 37° C. to 45° C.

15. The method of claim 1, wherein the reaction in step (1) occurs at about 45° C.

16. The method of claim 14, wherein the labeling precursor L1 substantially reacts with adducted nucleotides in the DNA relative to nucleotides comprising canonical nucleobases.

17. The method of claim 1, wherein the label L comprises one or more isotopes of H, C, O, or N in an amount exceeding or less than the natural abundance.

18. The method of claim 1, wherein the DNA is human DNA.

19. A method for detecting the presence of a DNA adduct in DNA, comprising the following steps:
(1) reacting an adducted nucleobase in a nucleotide of the DNA with a labeling precursor L1 to provide an adducted nucleobase labeled with label L, wherein a nucleophilic moiety on the adducted nucleobase reacts with the labeling precursor L1;
(2) subjecting the DNA to neutral thermal hydrolysis to provide a free adducted nucleobase labeled with label L; and
(3) detecting the free adducted nucleobase labeled with label L by mass spectrometry,
wherein the label L comprises a quaternary amine group.

\* \* \* \* \*